(12) United States Patent
Holgate

(10) Patent No.: US 10,575,970 B2
(45) Date of Patent: *Mar. 3, 2020

(54) ROBOTIC DEVICE AND METHOD OF USING A PARALLEL MECHANISM

(71) Applicant: Össur Iceland ehf, Reykjavik (IS)

(72) Inventor: Matthew A. Holgate, Chandler, AZ (US)

(73) Assignee: Össur Iceland ehf, Reykjavik (IS)

( * ) Notice: Subject to any disclaimer, the term of this patent is extended or adjusted under 35 U.S.C. 154(b) by 58 days.

This patent is subject to a terminal disclaimer.

(21) Appl. No.: 15/379,815

(22) Filed: Dec. 15, 2016

(65) Prior Publication Data

US 2017/0095355 A1 Apr. 6, 2017

Related U.S. Application Data

(63) Continuation of application No. 14/081,857, filed on Nov. 15, 2013, now Pat. No. 9,532,877, which is a
(Continued)

(51) Int. Cl.
*A61F 2/64* (2006.01)
*A61F 2/66* (2006.01)
(Continued)

(52) U.S. Cl.
CPC .................. *A61F 2/68* (2013.01); *A61F 2/30* (2013.01); *A61F 2/3094* (2013.01); *A61F 2/60* (2013.01);
(Continued)

(58) Field of Classification Search
CPC ...... A61F 2/50; A61F 2/64; A61F 2/66; B25J 17/00
See application file for complete search history.

(56) References Cited

U.S. PATENT DOCUMENTS

| 909,859 A | 1/1909 | Apgar |
| 2,475,373 A | 7/1949 | Catranis |

(Continued)

FOREIGN PATENT DOCUMENTS

| CH | 543 277 | 12/1973 |
| CN | 2043873 U | 9/1989 |

(Continued)

OTHER PUBLICATIONS

Au, Samuel K. et al., "Biomechanical Design of a Powered Ankle-Foot Prosthesis," in Rehabilitation Robotics, 2007. ICORR 2007. IEEE 10th International Conference on, 2007, pp. 298-303.
(Continued)

*Primary Examiner* — Bruce E Snow
(74) *Attorney, Agent, or Firm* — Knobbe, Martens, Olson & Bear, LLP

(57) ABSTRACT

A parallel kinematically redundant device includes a base body portion and a movable portion. The movable portion includes first, second, and third joints. A first actuator is coupled to the first joint of the movable portion and to the base body portion. A second actuator is coupled in parallel with the first actuator between the second joint of the movable portion and the base body portion. A linking member is rotationally coupled to the third joint of the movable portion to provide an output for the first and second actuators. A housing is coupled to the base body portion and fits onto a user. A prosthetic joint device includes a base portion and a movable portion. An actuator is rotationally coupled to the movable portion and base portion. A compliant element is coupled in parallel with the actuator between the movable portion and base portion.

25 Claims, 15 Drawing Sheets

Related U.S. Application Data continuation-in-part of application No. 13/673,177, filed on Nov. 9, 2012, now Pat. No. 9,604,368.

(60) Provisional application No. 61/558,761, filed on Nov. 11, 2011.

(51) Int. Cl.

| | | |
|---|---|---|
| B25J 17/00 | (2006.01) | |
| A61F 2/68 | (2006.01) | |
| A61F 2/30 | (2006.01) | |
| B25J 19/00 | (2006.01) | |
| A61F 2/60 | (2006.01) | |
| A61F 2/50 | (2006.01) | |
| A61F 2/70 | (2006.01) | |
| A61F 2/74 | (2006.01) | |

(52) U.S. Cl.
CPC ............ *A61F 2/66* (2013.01); *B25J 19/0091* (2013.01); *A61F 2002/5006* (2013.01); *A61F 2002/5072* (2013.01); *A61F 2002/607* (2013.01); *A61F 2002/701* (2013.01); *A61F 2002/704* (2013.01); *A61F 2002/745* (2013.01); *A61F 2002/747* (2013.01); *Y10T 29/49826* (2015.01)

(56) References Cited

U.S. PATENT DOCUMENTS

| | | |
|---|---|---|
| 2,568,051 A | 9/1951 | Catranis |
| 3,045,247 A | 7/1962 | Bair |
| 3,557,387 A | 1/1971 | Ohlenbusch et al. |
| 3,589,134 A | 6/1971 | Hackmann |
| 3,871,032 A | 3/1975 | Karas |
| 3,953,900 A | 5/1976 | Thompson |
| 3,995,324 A | 12/1976 | Burch |
| 4,030,141 A | 6/1977 | Graupe |
| 4,209,860 A | 7/1980 | Graupe |
| 4,387,472 A | 6/1983 | Wilson |
| 4,488,320 A | 12/1984 | Wilson |
| 4,579,558 A | 4/1986 | Ramer |
| 4,652,266 A | 3/1987 | Truesdell |
| 4,776,852 A | 10/1988 | Rubic |
| 4,805,455 A | 2/1989 | DelGiorno et al. |
| 5,020,790 A | 6/1991 | Beard et al. |
| 5,062,673 A | 11/1991 | Mimura |
| 5,101,472 A | 3/1992 | Repperger |
| 5,156,630 A | 10/1992 | Rappoport et al. |
| 5,201,772 A | 4/1993 | Maxwell |
| 5,246,465 A | 9/1993 | Rincoe et al. |
| 5,252,102 A | 10/1993 | Singer et al. |
| 5,252,901 A | 10/1993 | Ozawa et al. |
| 5,282,460 A | 2/1994 | Boldt |
| 5,376,138 A | 12/1994 | Bouchard et al. |
| 5,376,141 A | 12/1994 | Phillips |
| 5,383,939 A | 1/1995 | James |
| 5,413,611 A | 5/1995 | Haslam, II et al. |
| 5,425,780 A | 6/1995 | Flatt et al. |
| 5,430,643 A | 7/1995 | Seraji |
| 5,443,528 A | 8/1995 | Allen |
| 5,455,497 A | 10/1995 | Hirose et al. |
| 5,484,389 A | 1/1996 | Stark et al. |
| 5,571,205 A | 11/1996 | James |
| 5,650,704 A | 7/1997 | Pratt et al. |
| 5,662,693 A | 9/1997 | Johnson et al. |
| 5,695,527 A | 12/1997 | Allen |
| 5,800,570 A | 9/1998 | Collier |
| 5,888,212 A | 3/1999 | Petrofsky et al. |
| 5,888,213 A | 3/1999 | Sears et al. |
| 5,893,891 A | 4/1999 | Zahedi |
| 5,929,332 A | 7/1999 | Brown |
| 5,948,021 A | 9/1999 | Radcliffe |
| 5,954,621 A | 9/1999 | Joutras et al. |
| 5,957,981 A | 9/1999 | Gramnaes |
| 5,984,972 A | 11/1999 | Huston et al. |
| 6,029,374 A | 2/2000 | Herr et al. |
| 6,086,616 A | 7/2000 | Okuda et al. |
| 6,091,977 A | 7/2000 | Tarjan et al. |
| 6,117,177 A | 9/2000 | Chen et al. |
| 6,122,960 A | 9/2000 | Hutchings et al. |
| 6,129,766 A | 10/2000 | Johnson et al. |
| 6,187,052 B1 | 2/2001 | Molino et al. |
| 6,206,932 B1 | 3/2001 | Johnson |
| 6,378,190 B2 | 4/2002 | Akeel |
| 6,379,393 B1 | 4/2002 | Mavroidis et al. |
| 6,423,098 B1 | 7/2002 | Biedermann |
| 6,436,149 B1 | 8/2002 | Rincoe |
| 6,443,993 B1 | 9/2002 | Koniuk |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,517,858 B1 | 2/2003 | Le Moel et al. |
| 6,522,266 B1 | 2/2003 | Soehren et al. |
| 6,543,987 B2 | 4/2003 | Ehrat |
| 6,587,728 B2 | 7/2003 | Fang et al. |
| 6,610,101 B2 | 8/2003 | Herr et al. |
| 6,613,097 B1 | 9/2003 | Cooper |
| 6,645,252 B2 | 11/2003 | Asai et al. |
| 6,679,920 B2 | 1/2004 | Biedermann et al. |
| 6,695,885 B2 | 2/2004 | Schulman et al. |
| 6,704,024 B2 | 3/2004 | Robotham et al. |
| 6,704,582 B2 | 3/2004 | Le-Faucheur et al. |
| 6,719,807 B2 | 4/2004 | Harris |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,764,521 B2 | 7/2004 | Molino et al. |
| 6,767,370 B1 | 7/2004 | Mosler et al. |
| 6,813,582 B2 | 11/2004 | Levi et al. |
| 6,824,569 B2 | 11/2004 | Okediji |
| 6,863,695 B2 | 3/2005 | Doddroe et al. |
| 6,875,241 B2 | 4/2005 | Christensen |
| 6,908,488 B2 | 6/2005 | Paasivaara et al. |
| 6,910,331 B2 | 6/2005 | Asai et al. |
| 6,955,692 B2 | 10/2005 | Grundei |
| 6,966,882 B2 | 11/2005 | Horst |
| 6,969,408 B2 | 11/2005 | Lecomte et al. |
| 7,029,500 B2 | 4/2006 | Martin |
| 7,066,964 B2 | 6/2006 | Wild |
| 7,112,938 B2 | 9/2006 | Takenaka et al. |
| 7,118,601 B2 | 10/2006 | Yasui et al. |
| 7,137,998 B2 | 11/2006 | Bédard et al. |
| 7,147,667 B2 | 12/2006 | Bédard et al. |
| 7,150,762 B2 | 12/2006 | Caspers |
| 7,164,967 B2 | 1/2007 | Etienne-Cummings et al. |
| 7,182,738 B2 | 2/2007 | Bonutti et al. |
| 7,209,788 B2 | 4/2007 | Nicolelis et al. |
| 7,279,009 B2 | 10/2007 | Herr et al. |
| 7,295,892 B2 | 11/2007 | Herr et al. |
| 7,300,240 B2 | 11/2007 | Brogardh |
| 7,308,333 B2 | 12/2007 | Kern et al. |
| 7,313,463 B2 | 12/2007 | Herr et al. |
| 7,314,490 B2 | 1/2008 | Bédard et al. |
| 7,381,192 B2 | 6/2008 | Brodard et al. |
| 7,396,337 B2 | 7/2008 | McBean et al. |
| 7,410,471 B1 | 8/2008 | Campbell et al. |
| 7,431,737 B2 | 10/2008 | Ragnarsdottir et al. |
| 7,455,696 B2 | 11/2008 | Bisbee, III et al. |
| 7,462,201 B2 | 12/2008 | Christensen |
| 7,485,152 B2 | 2/2009 | Haynes et al. |
| 7,520,904 B2 | 4/2009 | Christensen |
| 7,531,006 B2 | 5/2009 | Clausen et al. |
| 7,552,664 B2 | 6/2009 | Bulatowicz |
| 7,575,602 B2 | 8/2009 | Amirouche et al. |
| 7,578,799 B2 | 8/2009 | Thorsteinsson et al. |
| 7,637,957 B2 | 12/2009 | Ragnarsdottir et al. |
| 7,637,959 B2 | 12/2009 | Clausen et al. |
| 7,655,050 B2 | 2/2010 | Palmer et al. |
| 7,691,154 B2 | 4/2010 | Asgeirsson et al. |
| 7,736,394 B2 | 6/2010 | Bédard et al. |
| 7,799,091 B2 | 9/2010 | Herr et al. |
| 7,811,333 B2 | 10/2010 | Jonsson et al. |

(56) References Cited

U.S. PATENT DOCUMENTS

| | | |
|---|---|---|
| 7,811,334 B2 | 10/2010 | Ragnarsdottir et al. |
| 7,815,689 B2 | 10/2010 | Bédard et al. |
| 7,867,284 B2 | 1/2011 | Bédard et al. |
| 7,896,927 B2 | 3/2011 | Clausen |
| 7,918,808 B2 | 4/2011 | Simmons |
| 7,942,935 B2 | 5/2011 | Iversen et al. |
| 7,955,398 B2 | 6/2011 | Bédard et al. |
| 7,985,265 B2 | 7/2011 | Moser et al. |
| 7,992,849 B2 | 8/2011 | Sugar et al. |
| 8,011,229 B2 | 9/2011 | Lieberman et al. |
| 8,048,007 B2 | 11/2011 | Roy |
| 8,048,172 B2 | 11/2011 | Jonsson et al. |
| 8,057,550 B2 | 11/2011 | Clausen et al. |
| 8,075,633 B2 | 12/2011 | Herr et al. |
| 8,083,807 B2 | 12/2011 | Auberger et al. |
| 8,109,890 B2 | 2/2012 | Kamiar et al. |
| 8,142,370 B2 | 3/2012 | Weinberg et al. |
| 8,202,325 B2 | 6/2012 | Albrecht-Laatsch et al. |
| 8,231,687 B2 | 7/2012 | Bédard et al. |
| 8,287,477 B1 | 10/2012 | Herr et al. |
| 8,322,695 B2 | 12/2012 | Sugar et al. |
| 8,323,354 B2 | 12/2012 | Bédard et al. |
| 8,376,971 B1 | 2/2013 | Herr et al. |
| 8,403,997 B2 | 3/2013 | Sykes et al. |
| 8,419,804 B2 | 4/2013 | Herr et al. |
| 8,435,309 B2 | 5/2013 | Gilbert et al. |
| 8,480,760 B2 | 7/2013 | Hansen et al. |
| 8,500,823 B2 | 8/2013 | Herr et al. |
| 8,500,825 B2 | 8/2013 | Christensen et al. |
| 8,512,415 B2 | 8/2013 | Herr et al. |
| 8,551,184 B1 | 10/2013 | Herr |
| 8,601,897 B2 | 12/2013 | Lauzier et al. |
| 8,617,254 B2 | 12/2013 | Bisbee, III et al. |
| 8,657,886 B2 | 2/2014 | Clausen et al. |
| 8,696,764 B2 | 4/2014 | Hansen et al. |
| 8,702,811 B2 | 4/2014 | Ragnarsdottir et al. |
| 7,896,927 C1 | 5/2014 | Clausen et al. |
| 8,716,877 B2 | 5/2014 | Sugar et al. |
| 8,734,528 B2 | 5/2014 | Herr et al. |
| 8,764,850 B2 | 7/2014 | Hanset et al. |
| 8,790,282 B2 | 7/2014 | Jung et al. |
| 8,801,802 B2 | 8/2014 | Oddsson et al. |
| 8,814,949 B2 | 8/2014 | Gramnaes |
| 8,852,292 B2 | 10/2014 | Ragnarsdottir et al. |
| 8,864,846 B2 | 10/2014 | Herr et al. |
| 8,870,967 B2 | 10/2014 | Herr et al. |
| 8,986,397 B2 | 3/2015 | Bédard et al. |
| 9,032,635 B2 | 5/2015 | Herr et al. |
| 9,044,346 B2 | 6/2015 | Langlois et al. |
| 9,060,883 B2 | 6/2015 | Herr et al. |
| 9,060,884 B2 | 6/2015 | Langlois |
| 9,066,819 B2 | 6/2015 | Gramnaes |
| 9,078,774 B2 | 7/2015 | Jónsson et al. |
| 9,114,029 B2 | 8/2015 | Ásgeirsson |
| 9,221,177 B2 | 12/2015 | Herr et al. |
| 9,271,851 B2 | 3/2016 | Claussen et al. |
| 9,289,316 B2 | 3/2016 | Ward et al. |
| 9,345,591 B2 | 5/2016 | Bisbee, III et al. |
| 9,345,592 B2 | 5/2016 | Herr et al. |
| 9,351,856 B2 | 5/2016 | Herr et al. |
| 9,358,137 B2 | 6/2016 | Bédard et al. |
| 9,459,698 B2 | 10/2016 | Lee |
| 9,462,966 B2 | 10/2016 | Clausen et al. |
| 9,498,401 B2 | 11/2016 | Herr et al. |
| 9,526,635 B2 | 12/2016 | Gilbert et al. |
| 9,526,636 B2 | 12/2016 | Bédard et al. |
| 9,532,877 B2 | 1/2017 | Holgate |
| 9,554,922 B2 | 1/2017 | Casler et al. |
| 9,561,118 B2 | 2/2017 | Clausen et al. |
| 9,604,368 B2 | 3/2017 | Holgate |
| 9,622,884 B2 | 4/2017 | Holgate et al. |
| 9,649,206 B2 | 5/2017 | Bédard |
| 9,682,005 B2 | 6/2017 | Herr et al. |
| 9,687,377 B2 | 6/2017 | Han et al. |
| 9,707,104 B2 | 7/2017 | Clausen |
| 9,717,606 B2 | 8/2017 | Gramnaes |
| 9,737,419 B2 | 8/2017 | Herr et al. |
| 9,808,357 B2 | 11/2017 | Langlois |
| 9,839,552 B2 | 12/2017 | Han et al. |
| 9,895,240 B2 | 2/2018 | Langlois et al. |
| 10,137,011 B2 | 11/2018 | Herr et al. |
| 10,195,057 B2 | 2/2019 | Clausen |
| 10,251,762 B2 | 4/2019 | Langlois |
| 10,299,943 B2 | 5/2019 | Clausen et al. |
| 10,307,271 B2 | 6/2019 | Holgate et al. |
| 10,369,019 B2 | 8/2019 | Clausen et al. |
| 2002/0007690 A1 | 1/2002 | Song et al. |
| 2002/0079857 A1 | 6/2002 | Ishii et al. |
| 2003/0005786 A1 | 1/2003 | Stuart et al. |
| 2004/0064195 A1 | 4/2004 | Herr |
| 2004/0078299 A1 | 4/2004 | Down-Logan et al. |
| 2004/0153484 A1 | 8/2004 | Unno |
| 2005/0049719 A1 | 3/2005 | Wilson |
| 2005/0049721 A1 | 3/2005 | Sulprizio |
| 2005/0070834 A1 | 3/2005 | Herr et al. |
| 2005/0107889 A1 | 5/2005 | Bédard et al. |
| 2005/0113973 A1 | 5/2005 | Endo et al. |
| 2005/0119763 A1 | 6/2005 | Christensen |
| 2005/0137717 A1 | 6/2005 | Gramnaes |
| 2005/0166685 A1 | 8/2005 | Boiten |
| 2005/0216097 A1 | 9/2005 | Rifkin |
| 2005/0283257 A1 | 12/2005 | Bisbee et al. |
| 2006/0025959 A1 | 2/2006 | Gomez et al. |
| 2006/0041321 A1 | 2/2006 | Christensen |
| 2006/0046907 A1 | 3/2006 | Rastegar et al. |
| 2006/0069336 A1 | 3/2006 | Krebs et al. |
| 2006/0069448 A1 | 3/2006 | Yasui |
| 2006/0184280 A1 | 8/2006 | Oddsson et al. |
| 2006/0189899 A1 | 8/2006 | Flaherty et al. |
| 2006/0249315 A1 | 11/2006 | Herr et al. |
| 2006/0259153 A1 | 11/2006 | Harn et al. |
| 2006/0260620 A1 | 11/2006 | Kazerooni et al. |
| 2007/0043449 A1 | 2/2007 | Herr et al. |
| 2007/0061016 A1 | 3/2007 | Kuo et al. |
| 2007/0123997 A1 | 5/2007 | Herr et al. |
| 2007/0129653 A1 | 6/2007 | Sugar et al. |
| 2007/0162152 A1 | 7/2007 | Herr et al. |
| 2008/0004718 A1 | 1/2008 | Mosler |
| 2008/0033578 A1 | 2/2008 | Christensen |
| 2008/0046096 A1 | 2/2008 | Bédard et al. |
| 2008/0058668 A1 | 3/2008 | Seyed Momen et al. |
| 2008/0141813 A1 | 6/2008 | Ehrat |
| 2008/0262635 A1 | 10/2008 | Moser et al. |
| 2008/0306612 A1 | 12/2008 | Mosler |
| 2009/0030530 A1 | 1/2009 | Martin |
| 2009/0088912 A1 | 4/2009 | Rajaraman |
| 2009/0192625 A1 | 7/2009 | Boiten |
| 2009/0204229 A1 | 8/2009 | Mosley et al. |
| 2009/0204230 A1 | 8/2009 | Kaltenborn et al. |
| 2009/0265018 A1 | 10/2009 | Goldfarb et al. |
| 2010/0023133 A1 | 1/2010 | Fairbanks et al. |
| 2010/0042228 A1 | 2/2010 | Doddroe et al. |
| 2010/0094431 A1 | 4/2010 | Albrecht-Laatsch |
| 2010/0113980 A1 | 5/2010 | Herr et al. |
| 2010/0114329 A1 | 5/2010 | Casler et al. |
| 2010/0131101 A1 | 5/2010 | Engeberg et al. |
| 2010/0161077 A1 | 6/2010 | Boone et al. |
| 2010/0174384 A1 | 7/2010 | Herr et al. |
| 2010/0185301 A1 | 7/2010 | Hansen et al. |
| 2010/0241242 A1 | 9/2010 | Herr et al. |
| 2010/0275718 A1 | 11/2010 | Stuart et al. |
| 2011/0015761 A1 | 1/2011 | Celebi et al. |
| 2011/0082566 A1 | 4/2011 | Herr et al. |
| 2011/0106274 A1 | 5/2011 | Ragnarsdottir et al. |
| 2011/0126660 A1 | 6/2011 | Lauzier et al. |
| 2011/0132131 A1 | 6/2011 | Worz |
| 2011/0137429 A1 | 6/2011 | Bédard et al. |
| 2011/0166674 A1 | 7/2011 | Montmartin |
| 2011/0196509 A1 | 8/2011 | Jansen et al. |
| 2011/0202144 A1 | 8/2011 | Palmer et al. |
| 2011/0208322 A1 | 8/2011 | Rifkin et al. |
| 2011/0295384 A1 | 12/2011 | Herr et al. |
| 2011/0295385 A1 | 12/2011 | Herr et al. |
| 2012/0078415 A1 | 3/2012 | Kubo et al. |

(56) References Cited

U.S. PATENT DOCUMENTS

| | | |
|---|---|---|
| 2012/0130508 A1 | 5/2012 | Harris et al. |
| 2012/0153875 A1 | 6/2012 | Glaister |
| 2012/0203359 A1 | 8/2012 | Schimmels et al. |
| 2012/0209405 A1 | 8/2012 | Herr et al. |
| 2012/0226364 A1 | 9/2012 | Kampas et al. |
| 2012/0259430 A1 | 10/2012 | Han et al. |
| 2012/0283845 A1 | 11/2012 | Herr et al. |
| 2012/0330439 A1 | 12/2012 | Goldfarb et al. |
| 2013/0006386 A1 | 1/2013 | Hansen et al. |
| 2013/0035769 A1 | 2/2013 | Bédard et al. |
| 2013/0046218 A1 | 2/2013 | Wiggin et al. |
| 2013/0142608 A1 | 6/2013 | Zhang et al. |
| 2013/0173022 A1 | 7/2013 | Arabian et al. |
| 2013/0218295 A1 | 8/2013 | Holgate et al. |
| 2013/0218298 A1 | 8/2013 | Mosler |
| 2013/0282141 A1 | 10/2013 | Herr et al. |
| 2013/0310979 A1 | 11/2013 | Herr et al. |
| 2014/0039642 A1 | 2/2014 | Nijiman et al. |
| 2014/0088730 A1 | 3/2014 | Hansen et al. |
| 2014/0114437 A1 | 4/2014 | Herr et al. |
| 2014/0121782 A1 | 5/2014 | Herr et al. |
| 2014/0191522 A1* | 7/2014 | Birglen ............ B25J 15/0009 294/106 |
| 2015/0032225 A1 | 1/2015 | Oddsson et al. |
| 2015/0073566 A1 | 3/2015 | Ragnarsdottir et al. |
| 2015/0127118 A1 | 5/2015 | Herr et al. |
| 2015/0164661 A1 | 6/2015 | Ragnarsdottir et al. |
| 2015/0209214 A1 | 7/2015 | Herr et al. |
| 2015/0265429 A1 | 9/2015 | Jónsson et al. |
| 2015/0328020 A1 | 11/2015 | Clausen et al. |
| 2016/0158031 A1 | 6/2016 | Ward et al. |
| 2016/0158032 A1 | 6/2016 | Ward et al. |
| 2016/0302956 A1 | 10/2016 | Gilbert et al. |
| 2017/0241497 A1 | 8/2017 | Mooney et al. |
| 2017/0304083 A1 | 10/2017 | Clausen |
| 2018/0125678 A1 | 5/2018 | Langlois |
| 2018/0177618 A1 | 6/2018 | Langlois |
| 2019/0175369 A1 | 6/2019 | Langlois |
| 2019/0224026 A1 | 7/2019 | Clausen |

FOREIGN PATENT DOCUMENTS

| | | |
|---|---|---|
| CN | 1215614 | 5/1999 |
| CN | 2400072 Y | 10/2000 |
| CN | 2776340 | 5/2006 |
| DE | 3923057 A1 | 1/1991 |
| DE | 42 29 330 | 3/1994 |
| EP | 0 358 056 | 3/1990 |
| EP | 0 380 060 | 8/1990 |
| EP | 0 718 951 | 6/1996 |
| EP | 1 107 420 | 6/2001 |
| EP | 1 169 982 | 1/2002 |
| EP | 1 410 780 | 4/2004 |
| EP | 1 442 704 | 8/2004 |
| EP | 1 547 567 | 6/2005 |
| EP | 1 718 252 | 11/2006 |
| EP | 1 792 597 | 6/2007 |
| EP | 2 564 817 | 3/2013 |
| EP | 2 702 963 | 3/2014 |
| FR | 2 816 463 | 5/2002 |
| GB | 2 201 260 | 8/1988 |
| GB | 2 228 201 | 8/1990 |
| GB | 2 260 495 | 4/1993 |
| GB | 2 301 776 | 12/1996 |
| GB | 2 302 949 | 2/1997 |
| GB | 2 367 753 | 4/2002 |
| JP | 59-032453 | 2/1984 |
| JP | 59-071747 | 4/1984 |
| JP | 59-088147 | 5/1984 |
| JP | 59-189843 | 10/1984 |
| JP | 60-177102 | 9/1985 |
| JP | 05-123348 | 5/1993 |
| JP | 05-161668 | 6/1993 |
| JP | 07-024766 | 1/1995 |
| JP | 11-215793 | 8/1999 |
| JP | 2002-191654 | 7/2002 |
| JP | 2005-536317 | 12/2005 |
| JP | 2009-153660 | 7/2009 |
| KR | 2002-0041137 | 6/2002 |
| SU | 1447366 | 12/1988 |
| SU | 1731210 | 5/1992 |
| WO | WO 94/009727 | 5/1994 |
| WO | WO 96/041599 | 12/1996 |
| WO | WO 97/027822 | 8/1997 |
| WO | WO 00/027318 | 5/2000 |
| WO | WO 03/003953 | 1/2003 |
| WO | WO 03/088373 | 10/2003 |
| WO | WO 2004/017890 | 3/2004 |
| WO | WO 2006/024876 | 3/2006 |
| WO | WO 2006/076164 | 7/2006 |
| WO | WO 2007/025116 | 3/2007 |
| WO | WO 2007/095933 | 8/2007 |
| WO | WO 2008/080231 | 7/2008 |
| WO | WO 2010/027968 | 3/2010 |
| WO | 2011005482 A2 | 1/2011 |
| WO | 2011096965 A2 | 8/2011 |
| WO | WO 2012/062279 | 5/2012 |
| WO | 2012091555 A1 | 7/2012 |
| WO | WO 2013/006585 | 1/2013 |
| WO | 2013086035 A1 | 6/2013 |
| WO | WO 2015/157723 | 10/2015 |

OTHER PUBLICATIONS

Au, Samuel K. et al., "Powered Ankle—Foot Prosthesis Improves Walking Metabolic Economy," Robotics, IEEE Transactions on, vol. 25, pp. 51-66, 2009.

Au, Samuel K. et al., "Powered Ankle-Foot Prosthesis for the Improvement of Amputee Ambulation," in Engineering in Medicine and Biology Society, 2007. EMBS 2007. 29th Annual International Conference of the IEEE, 2007, p. 3020.

Au, Samuel K. et al. "Powered ankle-foot prosthesis to assist level-ground and stair-descent gaits," Neural Networks, 21, 2008, pp. 654.666.

Au, Samuel K. et al., "Powered ankle-foot prosthesis," Robotics & Automation Magazine, IEEE, vol. 15, pp. 52-59, 2008.

Au, Samuel K., "Powered Ankle-Foot Prosthesis for the Improvement of Amputee Walking Economy," Massachusetts Institute of Technology, 2007, pp. 1-108.

Belforte, G. et. al., "Pneumatic Active Gait Orthosis". Mechatronics 11, 2001, pp. 301-323.

Bellman, Ryan D. et al., "SPARKy 3: Design of an Active Robotic Ankle Prosthesis with two Actuated Degrees of Freedom Using Regenerative Kinetics", 2nd IEEE RAS & EMBS International Conference on Biomedical Robotics and Biomechatronics, pp. 511-516, 2008.

Bernardi, M. et al., (1995), "The Efficiency of Walking of Paraplegic Patients Using a Reciprocating Gait Orthosis," Spinal Cord 33(7): 409-415.

Boehler, Alexander W. et al., (2008), "Design, Implementation and Test Results of a Robust Control Algorithm for a Powered Ankle Foot Orthosis," IEEE International Conference on Robotics and Automation (ICRA), IEEE.

Colombo, Gery et. al., "Treadmill Training of Paraplegic Patients Using a Robotic Orthosis", Journal of Rehabilitation Research and Development. vol. 37 No. 6., 2000, pp. 693-700.

Farley, Claire et al., "Biomechanics of Walking and Running: Center of Mass Movements to Muscle Action," Exerc Sport Sci Rev, vol. 26, pp. 253-285, 1998.

Guiraud, D., "Application of an Artificial Neural Network to the Control of an Active External Orthosis of the Lower Limb", Medical & Biological Engineering & Computing, Nov. 1994, vol. 32, pp. 610-614.

Hansen, Andrew H. et al., "The Effects of Prosthetic Foot Roll-over Shape Arc Length on the Gait of Trans-tibial Prosthesis Users," Prosthetics and Orthotics International, vol. 30, No. 3, 286-299, 2006.

(56) References Cited

OTHER PUBLICATIONS

Hansen, Andrew H. et al., "The human ankle during walking: implications for design of biomimetic ankle prostheses and orthoses," Journal of Biomechanics, 37(10): 1467-1474, 2004.

Hansen, Andrew H. et al., "Prosthetic ankle-foot mechanism capable of automatic adaptation to the walking surface," J Biomech Eng-T ASME, 131(3): 035002, 2009.

Herr, Hugh et al., "Patient-Adaptive Prosthetic and Orthotic Leg Systems", Proceedings of the International Federation for Medical & Biological Engineering, Reykjavik, Iceland, Jun. 18-22, 2002, pp. 18-21.

Hitt, Joseph et al., "A Robotic Transtibial Prothesis with Regenerative Kinetics: The Design Analyses, Methods, and Testing", U.S. Army Military Amputee Research Program, 2008.

Hitt, Joseph et al., "An Active Foot-Ankle Prosthesis with Biomechanical Energy Regeneration", Journal of Medical Devices, vol. 4, 2010.

Hitt, Joseph et al., (2010), "Bionic Running for Unilateral Transtibial Military Amputees," Proceedings of the 27th Army Science Conference, Orlando, FL.

Hitt, Joseph et al., (2010), "Dismounted Soldier Biomechanical Power Regeneration Kit (SPaRK)," Proceedings of the 27th Army Science Conference, Orlando, FL.

Hitt, Joseph et al., "Robotic Transtibial Prosthesis with Biomechanical Energy Regeneration", Industrial Robot: An International Journal, vol. 36, Issue 5, pp. 441-447, 2009.

Hitt, Joseph et al., "The SPARKy (Spring Ankle with Regenerative Kinetics) Project: Design and Analysis of a Robotic Transtibial Prosthesis with Regenerative Kinetics", ASME International Design Engineering Technical Conferences & Computers and Information in Engineering Conference (IDET/CIE), CD-ROM, pp. 1-10, 2007.

Holgate, Matthew A., "Control of a Robotic Transtibial Prosthesis", A Dissertation, Arizona State University, Dec. 2009.

Holgate, Matthew A. et al., "A Control Algorithm for a Prosthetic Ankle Using Phase Plane Invariants", Poster presentation at Dynamic Walking, Vancouver, Canada, 2009.

Holgate, Matthew A. et al., "A Novel Control Algorithm for Wearable Robotics Using Phase Plane Invariants", International Conference on Robotics and Automation, 2009.

Holgate, Matthew A. et al., "Control Algorithms for Ankle Robots: A Reflection on the State-of-the-Art and Presentation of Two Novel Algorithms", 2nd IEEE RAS & EMBS International Conference on Biomedical Robotics and Biomechatronics, pp. 97-103, 2008.

Holgate, Matthew A., "The SPARKy (Spring Ankle with Regenerative Kinetics) Project: Choosing a DC Motor Based Actuation Method" 2nd IEEE RAS & EMBS International Conference on Biomedical Robotics and Biomechatronics, pp. 163-168, 2008.

Hollander, Kevin W. et al., (2005), "A Robotic "Jack Spring" for Ankle Gait Assistance," DETC2005-84492, ASME ntemational Design Engineering Technical Conference (IDETC2005), Long Beach, CA, American Society of Mechanical Engineers.

Hollander, Kevin W. et al. "A Robust Control Concept for Robotic Ankle Gail Assistance," IEEE International Conference on Rehabilitation Robotics (ICORR), 2007, pp. 119-123.

Hollander, Kevin W. et al., (2006), "An Efficient Robotic Tendon for Gait Assistance," Journal of biomechanical engineering 128: 788.

Kawamoto, Hiroaki et al., (2003), "Power Assist Method for HAL-3 Estimating Operator's Intention Based on Motion Information," IEEE International Workshop on Robot and Human Interactive Communication, Millbrae, CA.

Kazerooni, H. et al., (2005), "On the Control of the Berkeley Lower Extremity Exoskeleton (BLEEX)," Proceedings of the 2005 IEEE International Conference on Robotics and Automation, Barcelona, Spain, Apr. 2005.

Kyriakopoulos K. et al., "Minimum jerk path generation." International Conference on Robotics and Automation, 1:364-369, 1988.

Norris, James A. et al., (2007), "Effect of Augmented Plantarflexion Power on Preferred Walking Speed and Economy in Young and Older Adults," Gait & Posture 25(4): 620-627.

Sawicki, Gregory S. et al., (2009), "It Pays to Have a Spring in your Step," Exercise and Sport Sciences Reviews 37(3).

Sawicki, Gregory S. et al., (2009), "Mechanics and Energetics of Incline Walking with Robotic Ankle Exoskeletons," Journal of Experimental Biology 212(1).

Sawicki, Gregory S. et al., (2009), "Powered Ankle Exoskeletons Reveal the Metabolic Cost of Plantar Flexor Mechanical Work During Walking with Longer Steps at Constant Step Frequency," Journal of Experimental Biology 212(1).

Sugar, Thomas G., (2002), "A Novel Selective Compliant Actuator," Mechatronics 12(9-10): 1157-1171.

Sup, Frank. et al., "Design and control of an active electrical knee and ankle prosthesis," in Biomedical Robotics and Biomechatronics, 2008. BioRob 2008. 2nd IEEE RAS & EMBS International Conference on, 2008, pp. 523-528.

Walsh, Conor James et al., (2006), Biomimetic Design of an Under-Actuated Leg Exoskeleton for Load-Carrying Augmentation, Cambridge, MA, Massachusetts Inst of Tech, M.S.

Walsh, Conor James et al., "Development of a Lightweight, Under-Actuated Exoskeleton for Load-Carrying Augmentation," Proceedings of the 2006 IEEE International Conference on Robotics and Automation, Orlando, Florida, May 2006.

Ward, Jeffrey et al., (2008), "Control Architectures for a Powered Ankle Foot Orthsosis," International Journal of Assistive Robotics and Mechatronics 9(2): 2-13.

Ward, Jeffrey et al., (2007), "Robotic Gait Trainer Reliability and Stroke Patient Case Study," IEEE 10th International Conference on Rehabilitation Robotics (ICORR), Holland.

Ward, Jeffrey et al., (2010), "Stroke Survivor Gait Adaptation and Performance After Training on a Powered Ankle Foot Orthosis," Proceedings of the IEEE International Conference on Robotics and Automation (ICRA), Anchorage, AK, IEEE.

Ward, Jeffrey et al., (2011), "Using the Translational Potential Energy of Springs for Prosthetic Systems," IEEE Multi-conference on Systems and Control, Denver, CO, IEEE.

Au et al., "An EMG-Position Controlled System for an Active Ankle-Foot Prosthesis: An Initial Experimental Study," Proceedings of the 2005 IEEE 9th International Conference on Rehabilitation Robotics, Chicago, IL, Jun. 28-Jul. 1, 2005, pp. 375-379.

Dietl et al., "Der Einsatz von Elektronik bei Prothesen zur Versorgung der unteren Extremität," Med. Orth. Tech., 1997, vol. 117, pp. 31-35.

DIGINFO TV, "Powered Prosthetic Thigh and Leg", uploaded Nov. 7, 2008 http://www.youtube.com/watch?v=lgitTzNEd54&feature=youtu.be%3E [Screenshots retrieved Oct. 23, 2014 in 9 pages].

"Extension Spring Design Theory, Spring Rate of Extension Springs," http://web.archive.org/web/20131209120508/http://springipedia.com/extension-design-theory.asp as archived Dec. 9, 2013 in 1 page.

Ficanha et al., "A Two-Axis Cable-Driven Ankle-Foot Mechanism", Robotics and Biometrics, 2014, vol. 1, No. 17, pp. 13.

Flowers et al., "An Electrohydraulic Knee-Torque Controller for a Prosthesis Simulator," Journal of Biomechanical Engineering: Transactions of the ASME; vol. 99, Series K, No. 1; Feb. 1977, pp. 3-8.

Hollander et al., "Adjustable Robotic Tendon using a 'Jack Spring'™", Proceedings of the 2005 IEEE 9th International Conference on Rehabilitation Robotics, Jun. 28-Jul. 1, 2005, Chicago, IL, pp. 113-118.

International Search Report and Written Opinion in International Application No. PCT/US2014/061913 dated Feb. 5, 2015 in 8 pages.

Martinez-Villalpando et al., "Agonist-Antagonist Active Knee Prosthesis: A Preliminary Study in Level-Ground Walking", Journal of Rehabilitation Research & Development, 2009, vol. 46, No. 3, pp. 361-373.

Mitchell et al., "Design and Development of Ankle-Foot Prosthesis with Delayed Release of Plantarflecion", Journal of Rehabilitation Research and Development, 2013, vol. 50, No. 3, pp. 409-422.

Mooney et al., "Design and Characterization of a Biologically Inspired Quasi-Passive Prosthetic Ankle-Foot", IEEE, 2014.

Realmuto et al., "Nonlinear Passive Cam-Based Springs for Powered Angle Prostheses", Journal of Medical Devices, Mar. 2015, vol. 9, pp. 011007-1-011007-10.

Robinson et al., "Series Elastic Actuator Development for a Biomimetic Walking Robot," MIT Leg Laboratory, 1999, pp. 1-8.

(56) References Cited

OTHER PUBLICATIONS

Townsend et al., "Biomechanics and Modeling of Bipedal Climbing and Descending," Journal of Biomechanics, vol. 9, No. 4, 1976, pp. 227-239.
Vanderborght et al., "MACCEPA 2.0: Adjustable Compliant Actuator with Stiffening Characteristic for Energy Efficient Hopping", 2009 IEEE International Conference on Robotics and Automation, Kobe International Conference Center, Kobe, Japan, May 12-17, 2009, pp. 544-549.
Wang et al., "Walk the Walk", IEEE Robotics & Automation Magazine, Aug. 26, 2015.

* cited by examiner

ROBOTIC DEVICE AND METHOD OF USING A PARALLEL MECHANISM

CLAIM TO DOMESTIC PRIORITY

The present application is a continuation of U.S. patent application Ser. No. 14/081,857, now U.S. Pat. No. 9,532,877, filed Nov. 15, 2013, which is a continuation-in-part of U.S. patent application Ser. No. 13/673,177, filed Nov. 9, 2012, which claims the benefit of U.S. Provisional Application No. 61/558,761, filed Nov. 11, 2011, which applications are incorporated herein by reference.

FIELD OF THE INVENTION

The present invention relates in general to robotic devices and, more particularly, to active and compliant artificial joints and limbs including a parallel mechanism.

BACKGROUND OF THE INVENTION

Prosthetic and orthotic devices help restore mobility to people who lack able-bodied motion or gait. Prosthetic devices are intended to replace the function or appearance of a missing limb and can return mobility to the wearer or user. Orthotic devices are intended to support or supplement an existing limb, by assisting with movement, reducing weight-bearing loads on the body, reducing pain, and controlling or restricting movement. Prosthetic and orthotic devices are available to replace or support various portions of the body. Lower limb prosthetic devices include, for example, the prosthetic foot, the foot-ankle prosthesis, the prosthetic knee joint, and the prosthetic hip joint. Lower limb orthotic devices include, for example, the foot orthoses, the ankle-foot orthoses, the knee-ankle-foot orthoses, and the knee orthoses. People who require a lower limb prosthesis or orthosis often expend more metabolic power to walk or move at the same speed as able-bodied individuals. One goal of lower limb prosthetic and orthotic devices is to help the user achieve a normal gait while reducing energy expended by the user.

Prosthetic and orthotic devices can be divided into two groups, passive devices and active devices. Passive lower limb prosthetics generally rely on compliant members, such as springs, to store and release energy. A spring is able to return only as much energy as is put into the spring. Thus, the energy that is released by a spring in a passive device is limited to the energy that is put in by the user. For example, a spring-based passive foot prosthetic provides about half of the peak power required for gait. The user of a passive device must expend additional energy through other muscles and joints to maintain a normal walking gait. Therefore, passive prosthetic and orthotic designs are limited in capacity to help users reduce metabolic energy expenditure while achieving a normal walking gait and performing other activities.

Active devices differ from passive devices in that active devices use a motor to supply power to the device and to control the device. Current active device designs are inefficient, either requiring relatively large motors, which are heavy and undesirable for wearable devices, or providing low peak power output, which is insufficient for many activities. Control systems for active devices are limited in capability to control active devices. Active prosthetics are typically restricted to a single degree of freedom, which reduces the motion available to the device. Further, active prosthetics are limited to low power activities, because the power necessary for high power activities is unattainable in a small portable system. One goal of active device designs is to increase efficiency of the active components and to build a lighter weight device.

Prosthetic devices are typically designed for a specific activity, such as walking. The majority of active compliant devices utilize a traditional rigid structure. The traditional rigid structure typically includes links powered by actuators such as electric motors or hydraulics. One strategy employs an architecture having a joint which is powered by a compliant member, such as a spring, and an active member, such as a motor driven screw, arranged in series. An activity-specific design strategy and traditional rigid structures may be suited for one specific activity, but the designs are limited in application and are not efficient beyond the intended activity. For example, devices designed for walking perform poorly for running, navigating uneven terrain, walking up and down inclines or stairs, or simply balancing while standing. Carrying heavy loads or transitioning from walking to running remains a challenge for users. Current active devices are ineffective for activities requiring both high velocities under low load and low velocities under high load. Another goal of prosthetic device designs is to perform more similarly to a human muscle during a variety of activities.

SUMMARY OF THE INVENTION

A need exists for prosthetic and orthotic devices that are better able to mimic the performance of human muscles over a wide range of activities. Accordingly, in one embodiment, the present invention is a method of making a prosthetic joint device comprising the steps of providing a base body, providing a movable body, disposing a first actuator connected between a first joint of the movable body and a first joint of the base body, disposing a second actuator in parallel with the first actuator and connected between a second joint of the movable body and a second joint of the base body, and disposing a passive linking member connected to a third joint of the movable body and further connected to a third joint of the base body. The second joint of the moveable body is disposed between the first joint of the moveable body and third joint of the moveable body to provide rotation of the passive linking member with respect to the base body.

In another embodiment, the present invention is a method of making a prosthetic joint device comprising the steps of providing a base body, providing a movable body, disposing a first linking member connected between a first joint of the movable body and a first joint of the base body, disposing a second linking member connected between a second joint of the movable body and a second joint of the base body, and disposing a passive linking member connected to a third joint of the movable body and further connected to a third joint of the base body to provide rotation of the passive linking member with respect to the base body.

In another embodiment, the present invention is a prosthetic joint device comprising a base body and movable body. A first actuator is connected between a first joint of the movable body and a first joint of the base body. A second actuator is connected between a second joint of the movable body and a second joint of the base body. A passive linking member is connected to a third joint of the movable body and further connected to a third joint of the base body to provide rotation of the passive linking member with respect to the base body.

In another embodiment, the present invention is a prosthetic joint device comprising a base body and movable body. A first linking member is connected between a first joint of the movable body and a first joint of the base body. A second linking member is connected between a second joint of the movable body and a second joint of the base body. A passive linking member is connected to a third joint of the movable body and further connected to a third joint of the base body to provide rotation of the passive linking member with respect to the base body.

BRIEF DESCRIPTION OF THE DRAWINGS

FIG. 9b illustrates a cut-away view of an active compliant device, according to the schematic representation shown in FIG. 9a;

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

An active prosthetic device is a wearable robotic device controlled by a computerized control system. The active prosthetic devices described herein incorporate parallel mechanisms to improve the performance of the devices. The parallel mechanisms couple springs and motors in a parallel kinematically redundant arrangement in order to provide prosthetic devices which behave more like human muscles.

Figure 1:
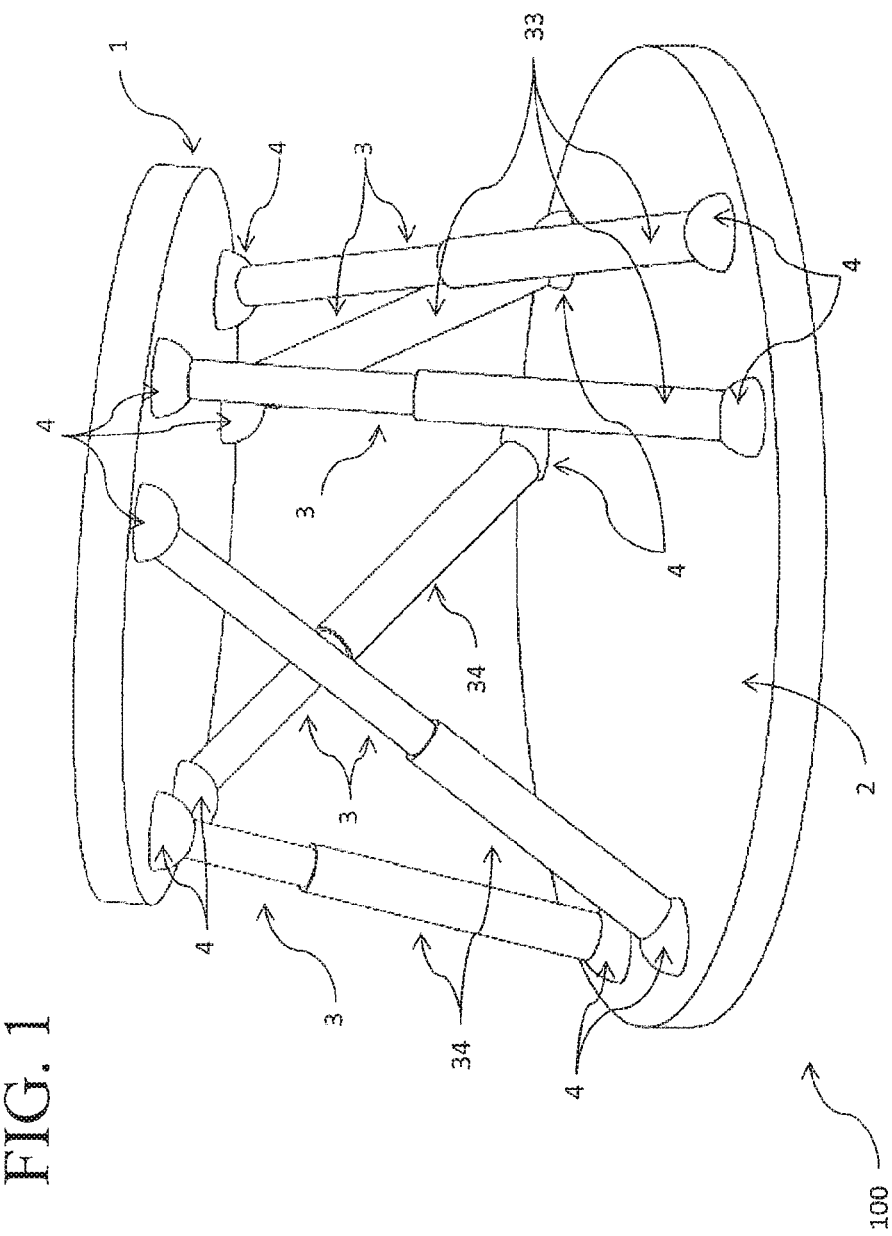
FIG. 1 illustrates a perspective view of a first active compliant parallel device.
Figure 2:
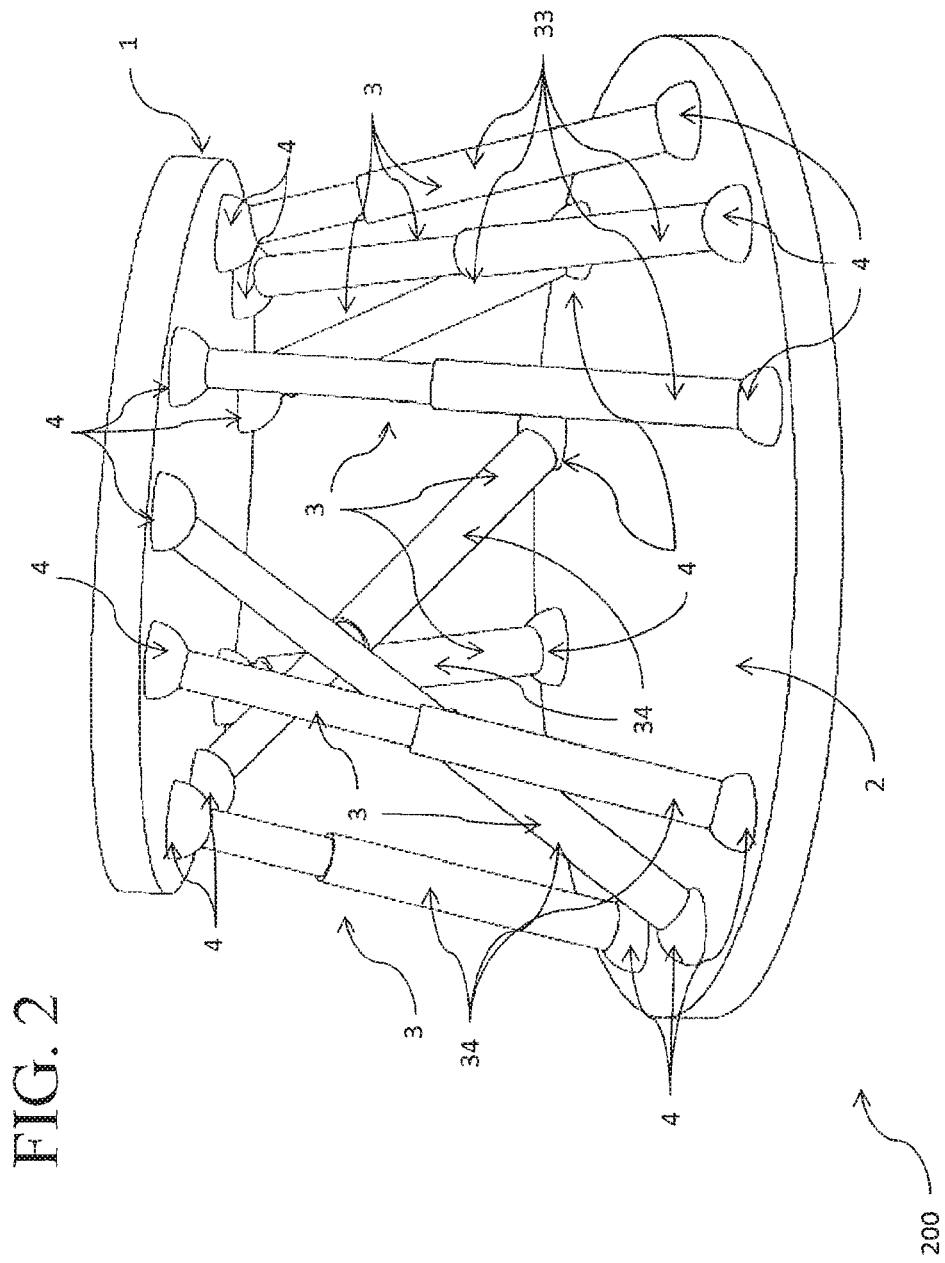
FIG. 2 illustrates a perspective view of a second active compliant parallel device.
Figure 3:
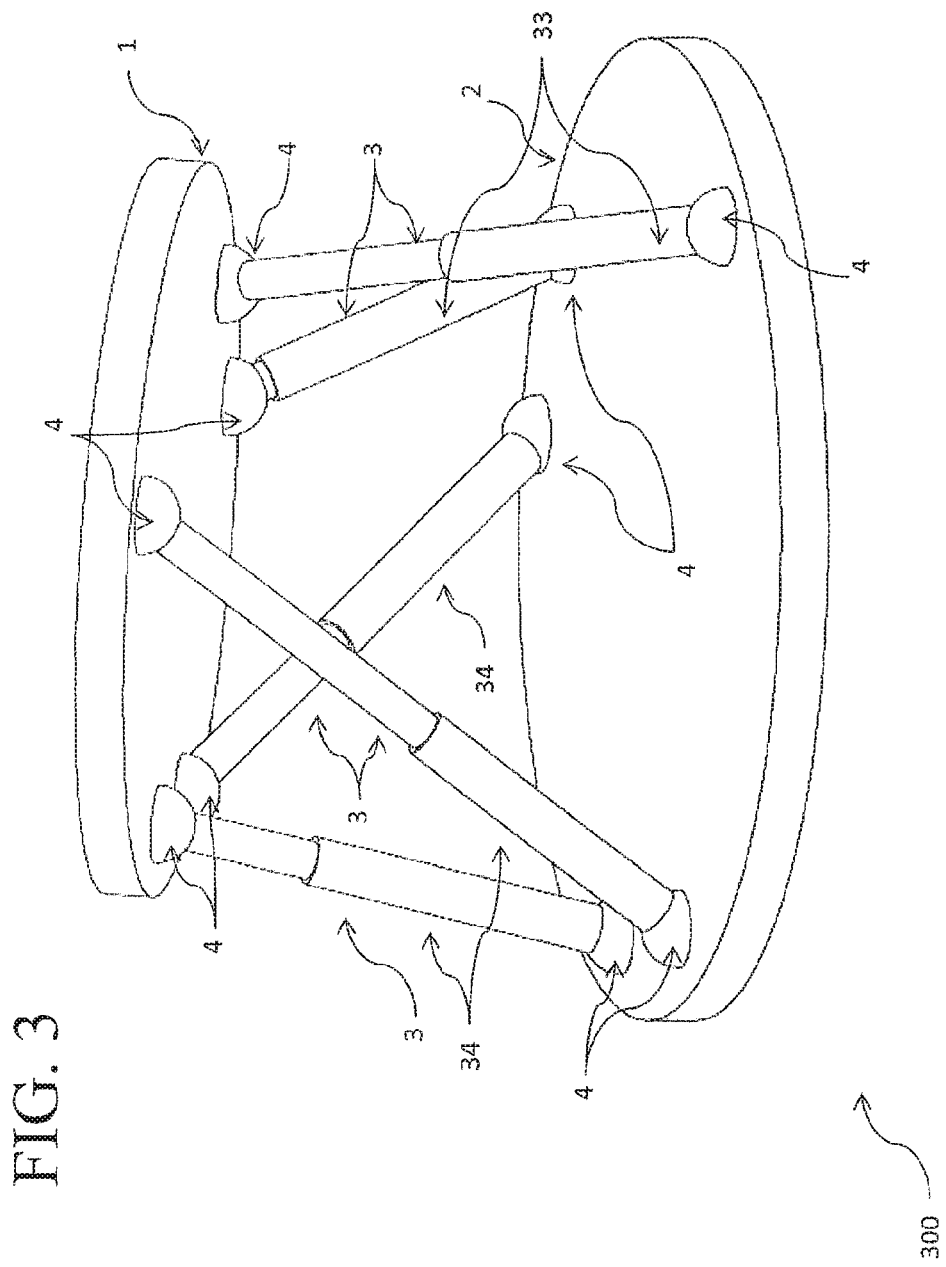
FIG. 3 illustrates a perspective view of a third active compliant parallel device.

FIGS. 1-3 illustrate active compliant parallel devices 100, 200, and 300 comprising a movable body 1, a base body 2, linking members 3, and connection elements 4. In parallel arrangement, movable body 1 is coupled to base body 2 by linking members 3. A parallel arrangement is defined as an arrangement where each linking member 3 is coupled to movable body 1 and base body 2, using connection elements 4. Thus, movable body 1 does not make a connection with base body 2 except through use of linking members 3.

Active compliant parallel devices 100, 200, and 300 move and position one or more elements in space when the element is both unrestricted and under external load. The element which active compliant parallel devices 100, 200, and 300 that move and position is movable body 1 or one or more linking members 3. Movable body 1 or one or more linking member 3 is considered an ultimate working member. An ultimate working member is a component that is the output of the device. Alternatively, movable body 1 or linking member 3 is coupled to one or more other bodies, which are working members by connection through one or more linking bodies. In another embodiment, the element which active compliant parallel devices 100, 200, and 300 move and position is a combination of movable body 1 and one or more linking members 3. Movable body 1 and one or more of linking members 3 are the ultimate working members. Alternatively, movable body 1 and linking members 3 is connected to one or more other bodies, which are the working members by connection through one or more additional linking bodies.

Linking members 3 shown in FIGS. 1-3 include at least one actuating linking member 33 and at least one compliant linking member 34. Linking members 3 optionally include any number of passive linking members (not shown) and any number of damping linking members (not shown). The linking members each apply from zero to five constraints on the degrees of freedom of the motion of movable body 1 with respect to base body 2.

Therefore, movable body 1 is linked to base body 2 by actuating linking members 33, compliant linking members 34, passive linking members, damping linking members, or a combination thereof. Actuating linking members 33, compliant linking members 34, passive linking members, or damping linking members are arranged in a parallel arrangement or structure, meaning each member makes a connection, using a connection element 4, with base body 2 and also with movable body 1. Actuating elements, compliant elements, or damping elements are applied to any of linking members 3 and can reside on the same linking member 3.

Each linking member 3 is a kinematic chain made up of bodies connected by various joint types. The joint types for linking members 3 include revolute joints, prismatic joints, screw-type joints, or other joint types. The joint type may further include one or more higher pair joint types, which are represented by a combination of revolute joints, prismatic joints, screw-type joints, or other joint types.

The kinematic freedom of movable body 1 with respect to base body 2 before being connected by linking members 3 is six, i.e., three translational degrees of freedom and three rotational degrees of freedom. Each linking member 3 is arranged so that its kinematic constraints of motion between base body 2 and movable body 1 are such that from zero to five kinematic freedoms are lost before the application of actuating, compliant, or damping elements to any of linking members 3. Each lost freedom is described instantaneously by a rotation, a translation, or a linear combination of a rotation and a translation.

One or more of the degrees of freedom of linking member 3 are controlled by actuating linking members 33, compliant linking members 34, and damping linking members. A controlled freedom is one that is regulated by a controlling element. The controlling element includes actuating, compliant, or damping elements, as determined by the type of linking member 3. A controlled freedom is not considered a constraint on the motion of movable body 1 with respect to base body 2 by linking member 3.

Actuating linking members 33 are configured such that one or more of the joints or the degrees of freedom of linking member 3 are controlled by an active component, such as a motor. Actuating linking members 33 are configured such that one or more of the joints of linking member 3 are actuated at the joint, or one or more of the joints of linking member 3 are replaced by an actuating element, or one or more of the degrees of freedom of linking member 3 are actuated across any number of the joints of linking member 3. An actuating element of actuating linking member 33 is any type of controllable position or force type actuator.

Compliant linking members 34 are configured such that one or more of the joints or the degrees of freedom of linking member 3 are controlled by a compliant element, such as a spring. Compliant linking members are configured such that one or more of the joints of linking member 3 are controlled by a compliant element, or one or more of the joints of linking member 3 are replaced by a compliant element, or one or more of the degrees of freedom of linking member 3 are controlled by a compliant element across any number of the joints of linking member 3. A compliant element of a compliant linking member 34 is a fixed rate compliant element, an adjustable variable rate compliant element, or a controllable variable rate compliant element.

Passive linking members are configured such that no joint of linking member 3 is regulated by a controlling element, no joint of the member is replaced by a controlling element, and no degree of freedom of linking member 3 is regulated by a controlling element.

Damping linking members are configured such that one or more of the joints or the degrees of freedom of linking member 3 are controlled by a damping component, such as a dashpot. Damping linking members are configured such that one or more of the joints of linking member 3 are controlled by a damping element, or one or more of the joints of linking member 3 are replaced by a damping element, or one or more of the degrees of freedom of linking member 3 are controlled by a damping element across any number of the joints of linking member 3. A damping element of a damping linking member is a fixed rate damping element, an adjustable variable rate damping element, or a controllable variable rate damping element.

Combination linking members are configured such that one or more of the joints of linking member 3 are controlled by an actuating, compliant, or damping element. Alternatively, one or more of the joints of the member are replaced by an actuating, compliant, or damping element. One or more of the degrees of freedom of linking member 3 are controlled by an actuating, compliant, or damping element across any number of the joints of linking member 3. Additional joints or the same joints of linking member 3 are controlled by a controlling element of a different type, replaced by a controlling element of a different type, or additional or the same degrees of freedom of linking member 3 are controlled by a controlling element of a different type.

An actuating element of a combination linking member is any type of controllable position or force type actuator. A compliant element of a combination linking member is a fixed rate compliant element, an adjustable variable rate compliant element, or a controllable variable rate compliant element. A damping element of a combination linking member is a fixed rate damping element, an adjustable variable rate damping element, or a controllable variable rate damping element.

By providing compliant linking members 34 in combination with actuating linking members 33 in a parallel arrangement, the structure allows for a change in geometry based on load, thereby effecting a change in transmission ratio of the input to the output of the device. Configurations with a combination of active and compliant linking members are especially adapted for applications where high velocities under low load are needed at times and low velocities under high load are needed at other times.

Linking members 3 are used to constrain motion of movable body 1 with respect to base body 2 so that the number of controlled freedoms, by actuation, compliance, or damping, of linking members 3 is equal to the number of freedoms afforded to movable body 1 with respect to base body 2 by linking members 3. In another embodiment, linking members 3 are used to constrain the motion of movable body 1 with respect to base body 2 so that the number of controlled freedoms, by actuation, compliance, or damping, of linking members 3 is greater than the number of freedoms afforded to movable body 1 with respect to base body 2 by linking members 3. In yet another embodiment, linking members 3 are used to constrain the motion of movable body 1 with respect to base body 2 so that the number of controlled freedoms, by actuation, compliance, or damping, of linking members 3 is less than the number of freedoms afforded to movable body 1 with respect to base body 2 by linking members 3. Therefore, by coupling movable body 1 in parallel with base body 2 with a combination of actuating, compliant, passive, and damping members, the geometry of the structure of active compliant parallel devices 100, 200, and 300 changes according to applied load. Because the geometry can be changed according to the applied load, the ratio of the output to the input of actuating linking members 33 is optimized for the task and type of actuators.

To achieve a desired behavior, the following properties are selected for the device: (1) the number of different types of linking members, (2) the arrangement and geometry of the kinematic chains that make up linking members 3, (3) the geometry of the connections, i.e., the connection locations on base body 2 and movable body 1, (4) the spring rates of compliant linking members 34, and (5) the damping rates of the damping linking members. The number and type of actuating linking members 33, compliant linking members 34, passive linking members, and damping linking members are determined by the desired degree of constraint or freedom from the active compliant parallel devices 100, 200, and 300.

Active compliant parallel devices 100, 200, and 300 provide for multiple advantages. One advantage, made possible by compliant linking members 34, is the change in geometry according to applied load. A change in geometry according to the applied load allows the position of the structure to change so that under high force or torque load, lower force or torque and higher speed is required of actuating linking members 33. Under low force or torque, higher force or torque and lower speed is required of actuating linking members 33. The result is an increased range in force or torque output and at the same time an increased range in speed. Through the parallel nature of the structure, a given load is distributed among linking members 3 resulting in lower loads for individual components. Because of the changing geometry, nonlinear spring behavior is more easily achievable. Spatial, as well as any lesser degree of freedom, compliant and actuating behavior is realized by choosing the number and constraints of linking members 3 to yield the desired properties.

Figure 4:
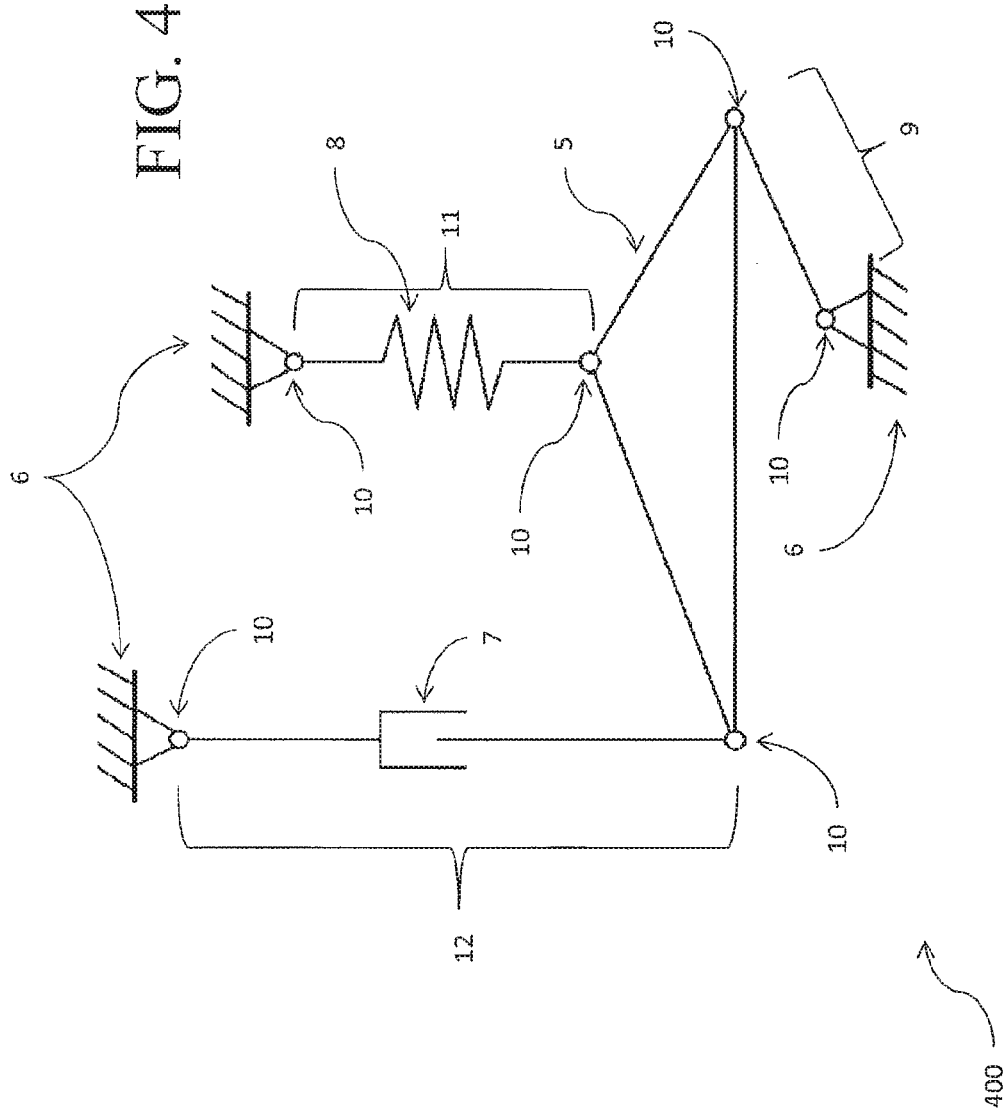
FIG. 4 illustrates a schematic representation of a first arrangement of an active compliant parallel device.

FIG. 1 shows a perspective view of an active compliant parallel device 100. The arrangement in FIG. 1 is considered a general configuration and is not by any means exhaustive in its representation of the embodiment. The constraint of the motion of movable body 1 in relation to base body 2 by linking members 3, which include actuating linking members 33 and compliant linking members 34, is such that the number of actuated freedoms plus the number of compliantly controlled freedoms is equal to the total freedom of the motion of movable body 1 in relation to base body 2.

Where damping linking members are included in active compliant parallel device 100, the number of actuated freedoms plus the number of compliantly controlled freedoms plus the number of damped freedoms is equal to the total freedom of the motion of movable body 1 in relation to base body 2 allowed by linking members 3. The result is that movable body 1 is fully controlled by linking members 3 in relation to base body 2 but not redundantly so. FIG. 4 shows an example of the arrangement in FIG. 1, as further described below.

Figure 5:
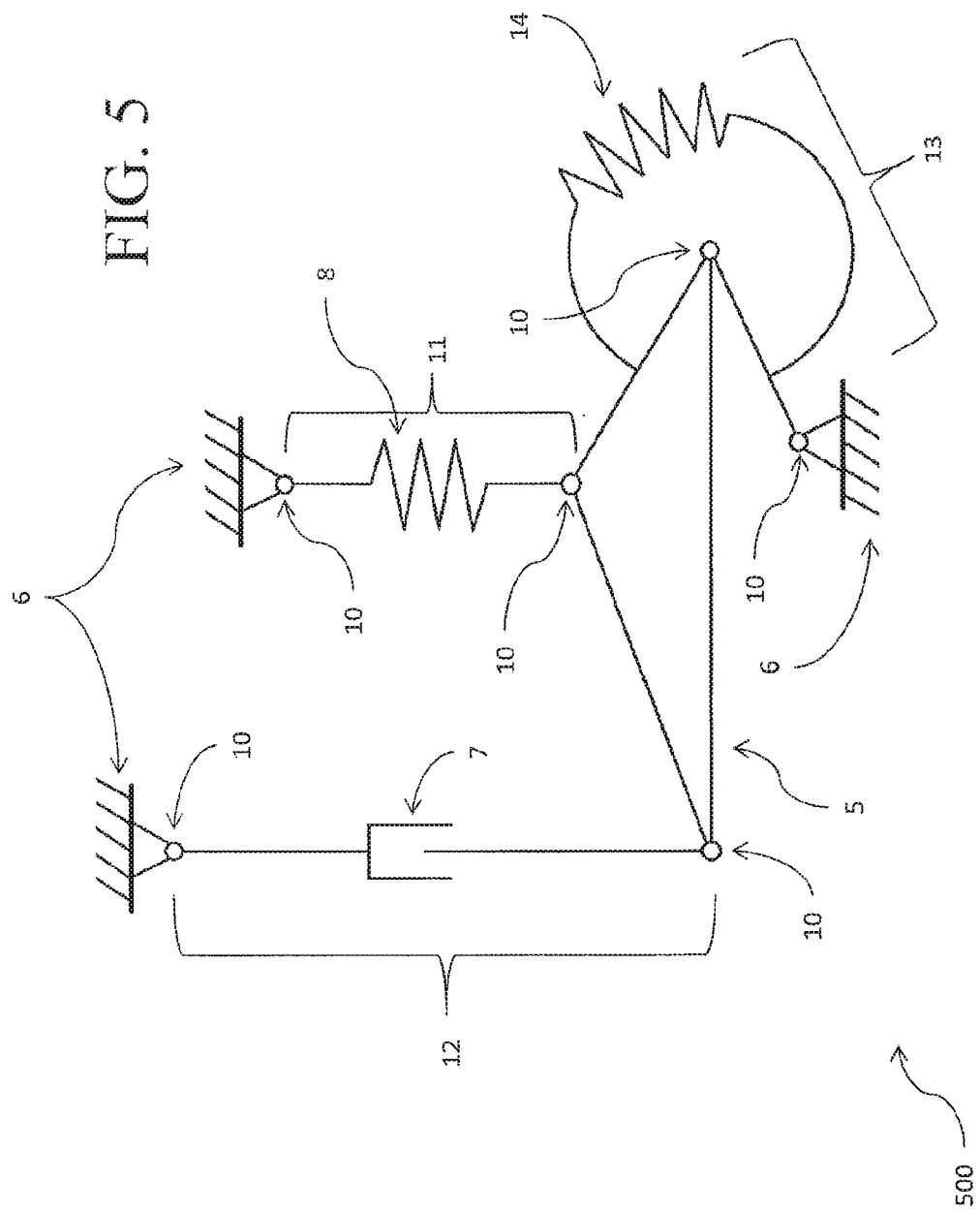
FIG. 5 illustrates a schematic representation of a second arrangement of an active compliant parallel device.

FIG. 2 shows a perspective view of an active compliant parallel device 200. The arrangement of active compliant parallel device 200 in FIG. 2 is considered a general configuration and is not by any means exhaustive in its representation of the embodiment. The constraint of the motion of movable body 1 in relation to base body 2 by linking members 3, which include actuating linking members 33 and compliant linking members 34, is such that the number of actuated freedoms plus the number of compliantly controlled freedoms is greater than the total freedom of the motion of movable body 1 in relation to base body 2.

Where damping members are included in device 200, constraint of the motion of movable body 1 in relation to base body 2 by linking members 3 is such that the number of actuated freedoms plus the number of compliantly controlled freedoms plus the number of damped freedoms is greater than the total freedom of the motion of movable body 1 in relation to base body 2 allowed by linking members 3. The result is that movable body 1 is fully controlled by linking members 3 in relation to base body 2 with a redundant amount of constraints. The redundant constraints are applied by actuating linking members 33, compliant linking members 34, passive linking members, damping linking members, or any combination of the same. An example of a qualifying arrangement is shown in FIG. 5, as further described below.

Figure 6:
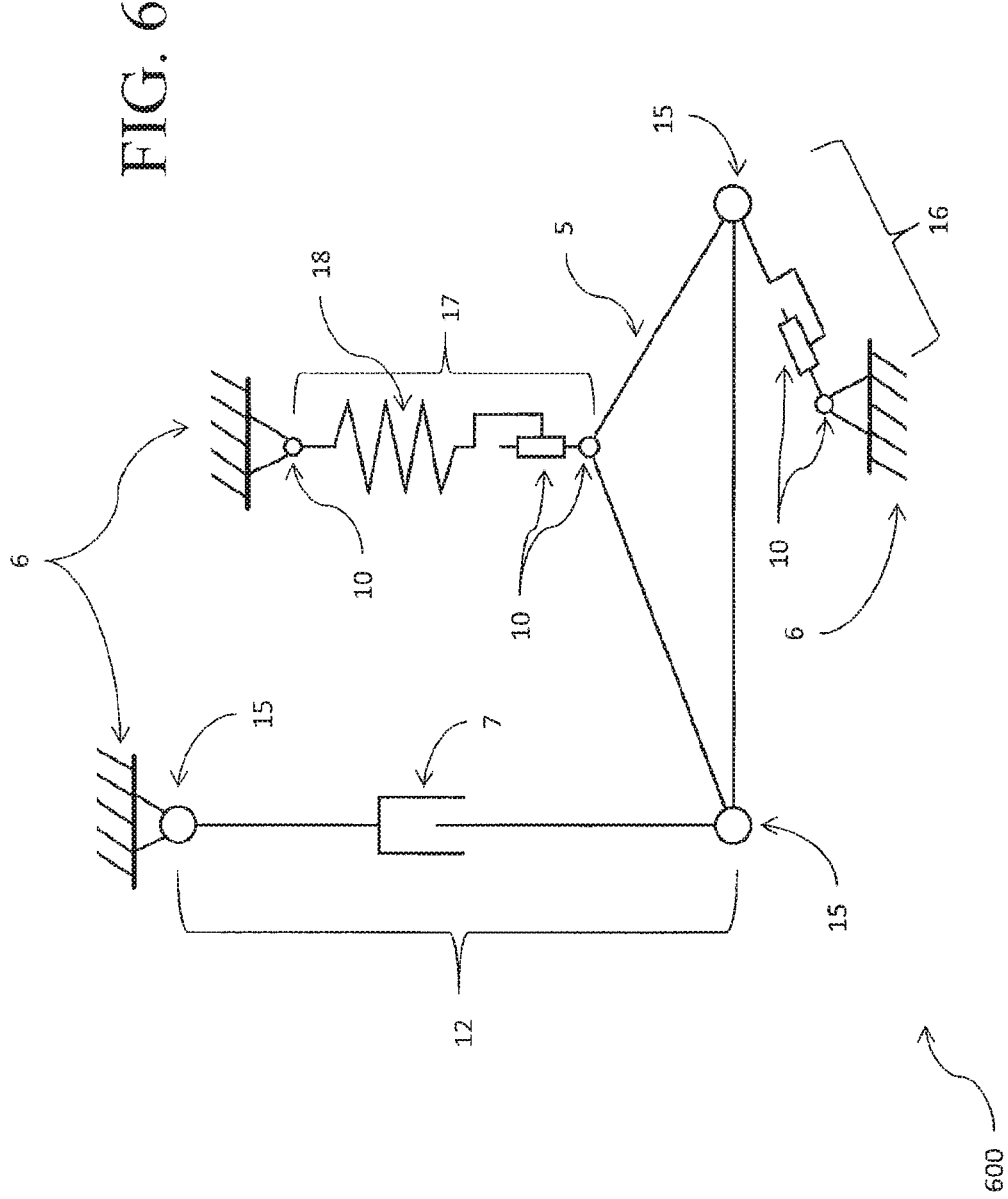
FIG. 6 illustrates a schematic representation of a third arrangement of an active compliant parallel device.

FIG. 3 shows a perspective view of an active compliant parallel device 300. The arrangement in FIG. 3 is considered a general configuration and is not by any means exhaustive in its representation of the embodiment. The constraint of the motion of movable body 1 in relation to base body 2 by linking members 3, which include actuating linking members 33 and compliant linking members 34, is such that the number of actuated freedoms plus the number of compliantly controlled freedoms is less than the total freedom of the motion of movable body 1 in relation to base body 2.

Where damping members are included in device 300, constraint of the motion of movable body 1 in relation to base body 2 by linking members 3 is such that the number of actuated freedoms plus the number of compliantly controlled freedoms plus the number of damped freedoms is less than the total freedom of the motion of movable body 1 in relation to base body 2 allowed by linking members 3. The result is that movable body 1 is not fully constrained with relation to base body 2. Thus, there exist degrees of freedom of movable body 1 in relation to base body 2 that are not constrained by any of actuating linking members 33, compliant linking members 34, or damping linking members. An example of a qualifying arrangement is shown in FIG. 6, as further described below.

FIG. 4 shows a schematic view of an arrangement of an active compliant parallel device 400. In the arrangement in FIG. 4, a movable body 5 is linked to base body 6 by a passive linking member 9, a compliant linking member 11, and actuating linking member 12. The linking members link movable body 5 to base body 6 by means of revolute joints 10 which have an axis that is normal to the plane of FIG. 4. FIG. 4 represents a schematic view of active compliant parallel device 100 from FIG. 1.

In FIG. 4, the actuating, compliant, or damping element of an actuating linking member 12, compliant linking member 11, or damping linking member is used to replace one or more of the joints of the linking member. The compliant linking member 11 has a compliant element 8 to control one of its degrees of freedom. Compliant element 8 acts as a prismatic joint. In an alternative embodiment, compliant element 8 is replaced with an actuating or damping element or the controlling element is replaced by a revolute, prismatic, screw-type joint or any higher pair joint that is a combination of a revolute, prismatic, screw-type joint. In addition, actuating linking member 12 is provided with an actuating element 7.

FIG. 5 shows a schematic view of active compliant parallel device 500 where movable body 5 is linked to base body 6 by compliant linking member 11, actuating linking member 12, and second compliant linking member 13. Compliant linking members 11, actuating linking member 12, and second compliant linking member 13 link movable body 5 to base body 6 by means of revolute joints 10 which have an axis that is normal to the plane of FIG. 5. Compliant linking member 11 includes a compliant element 8, while second compliant linking member 13 includes a second compliant element 14. In addition, actuating linking member 12 includes an actuating element 7. In another embodiment, compliant linking member 11 includes an actuating element in addition to a compliant element. In yet another embodiment, compliant linking member 11 is replaced with an actuating linking member, which includes an actuating element, such as a motor, instead of compliant element 8.

FIG. 6 shows a schematic view of active compliant parallel device 600 where movable body 5 is linked to base body 6 by actuating linking member 12, passive linking member 16, and compliant linking member 17. Actuating linking member 12, passive linking member 16, and compliant linking member 17 link movable body 5 to base body 6 by means of revolute joints 10 and spherical joints 15, where each has three rotational degrees of freedom. Spherical joints 15 are kinematically equivalent to three revolute joints, positioned so that their axes are normal to one another, and two prismatic joints, which are replaced by an actuating element and a compliant element. Before the actuating and compliant elements are applied, movable body 5 is constrained to have three kinematic freedoms with respect to base body 6 by the linking members. The sum of freedoms controlled by actuating, compliant, and damping elements is two, which is less than the three kinematic freedoms of movable body 5 with respect to base body 6.

Figure 7:
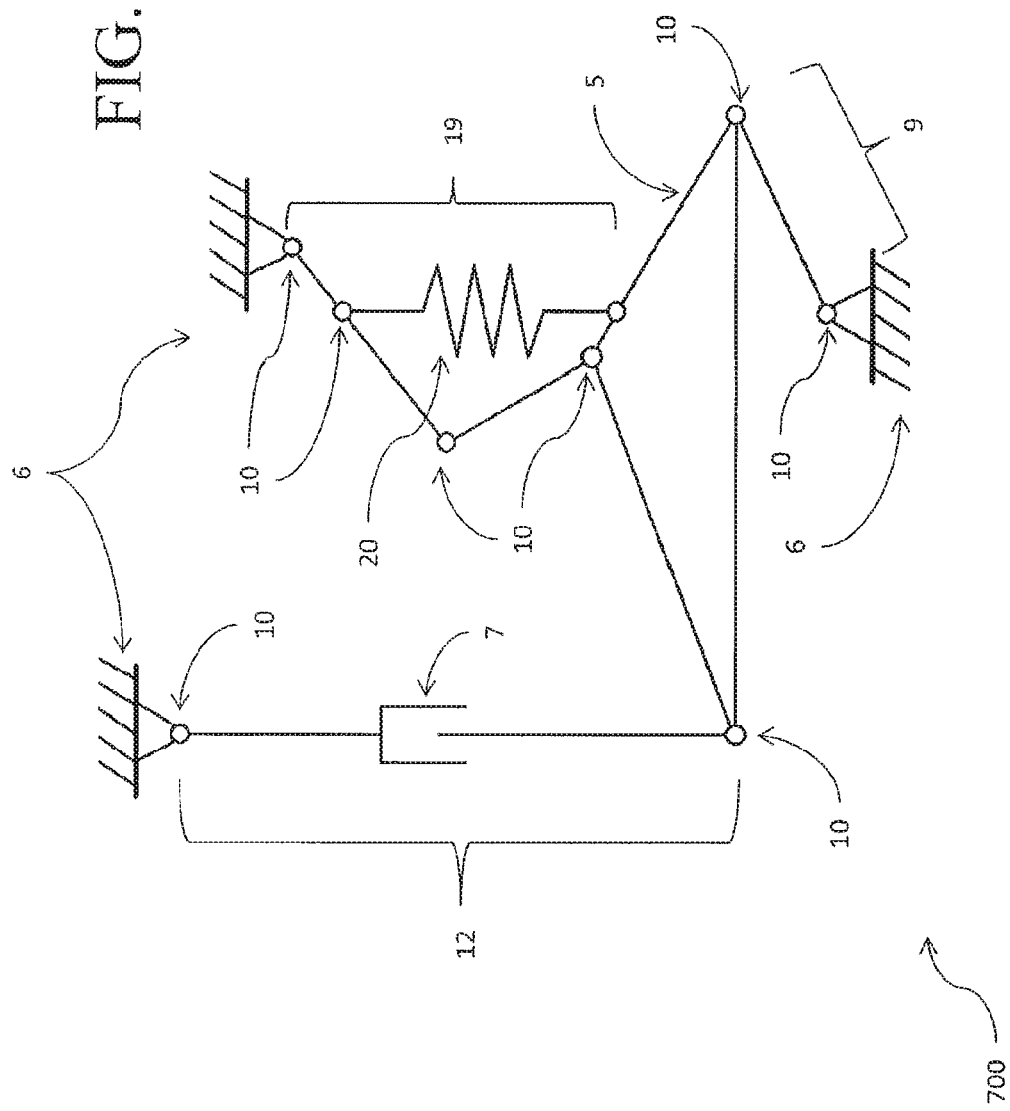
FIG. 7 illustrates a schematic representation of a fourth arrangement of an active compliant parallel device.

FIG. 7 shows a schematic view of active compliant parallel device 700 where movable body 5 is linked to base body 6 by means of passive linking member 9, actuating linking member 12, and compliant linking member 19. Passive linking member 9, actuating linking member 12, and compliant linking member 19 link movable body 5 to base body 6 by means of revolute joints 10, where each revolute joint 10 has an axis which is normal to the plane of FIG. 7. The compliant linking member 19 includes a compliant element 20, which is applied across a plurality of revolute joints 10 to provide connection points with movable body 5. In addition, the actuating linking member 12 includes an actuating element 7.

Figure 8:
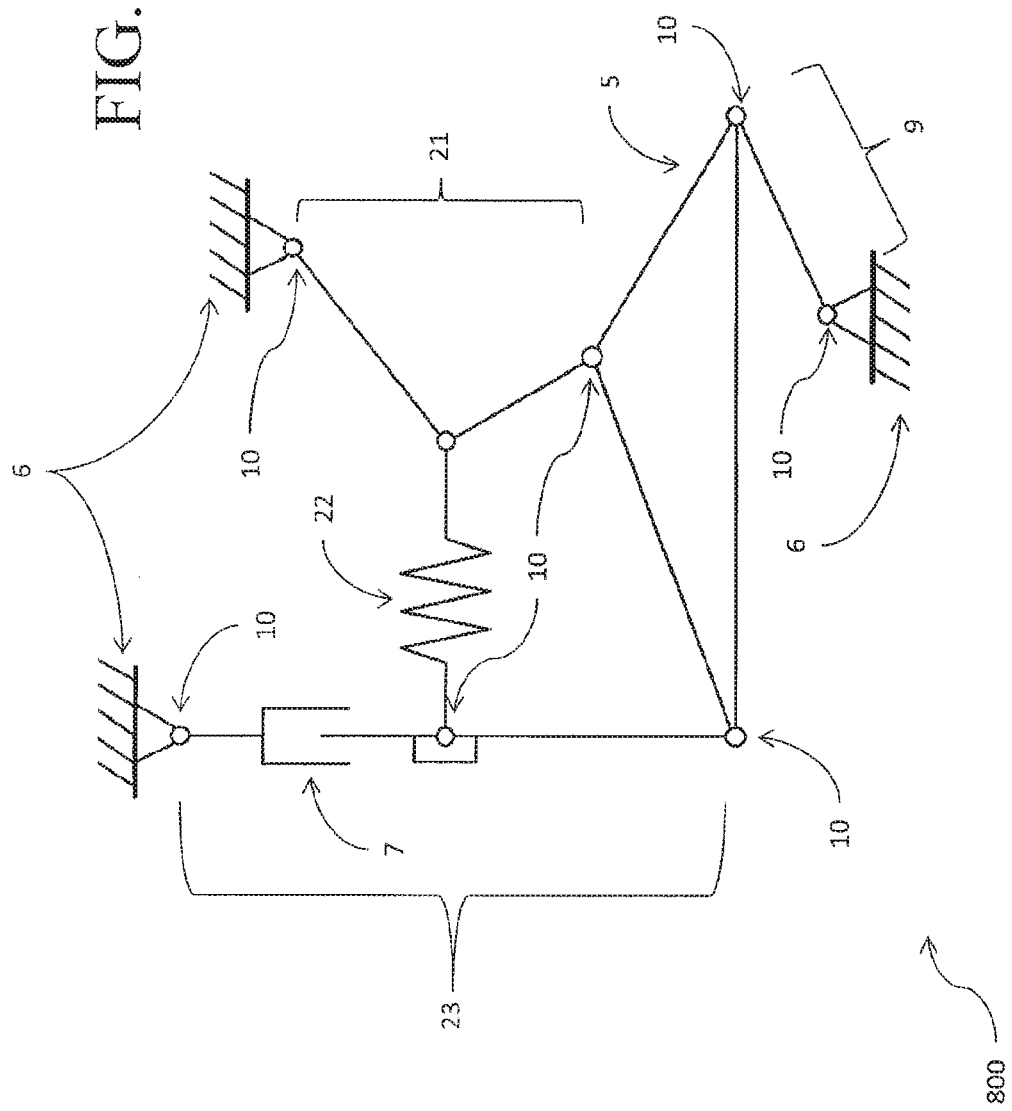
FIG. 8 illustrates a schematic representation of a fifth arrangement of an active compliant parallel device.

FIG. 8 shows a schematic view of active compliant parallel device 800 where movable body 5 is linked to base body 6 by passive linking member 9, compliant linking member 21 and actuating linking member 23. Passive linking member 9, compliant linking member 21 and actuating linking member 23 link movable body 5 to base body 6 by means of revolute joints 10, each having an axis which is normal to the plane of FIG. 8. The compliant linking member 21 includes a compliant element 22, which crosses over to the actuating linking member 23 though use of multiple revolute joints 10. In addition, actuating linking member 23 includes an actuating element 7.

Figure 9A:
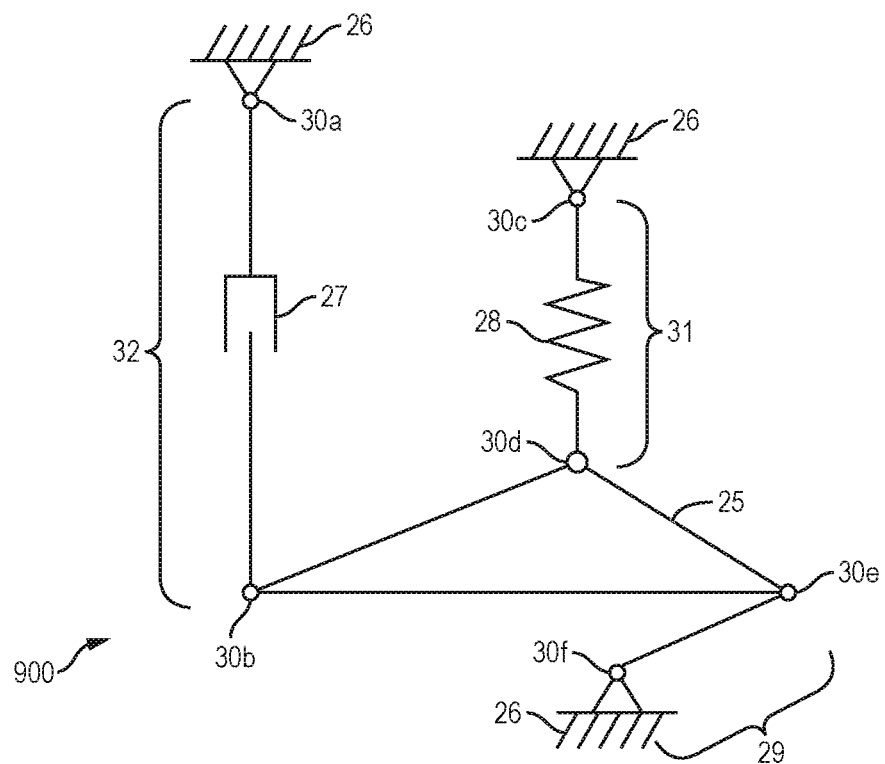
FIG. 9a illustrates a schematic representation of a sixth arrangement of an active compliant parallel device.

FIG. 9a shows a schematic view of an active compliant parallel mechanism or device 900, having an arrangement similar to active compliant parallel device 400 as shown in FIG. 4. Movable body 25 is linked to base body 26 by passive linking member 29, compliant linking member 31, and actuating linking member 32. Compliant linking member 31 and actuating linking member 32 are disposed in parallel between movable body 25 and base body 26. Therefore, compliant linking member 31 and actuating linking member 32 constitute the parallel mechanism of active compliant parallel device 900. Actuating linking member 32 includes actuating element 27, which is an electric motor and lead screw or ball, hydraulic, pneumatic, direct-drive, series-elastic, electroactive polymer-based, chemical-based, or other actuation scheme. Compliant linking member 31 includes compliant element 28, which can be a helical or coil spring.

Base body 26 represents the fixed portions within active compliant parallel device 900 to which the movable members are attached. Base body 26 is fixed with respect to the user, while the device as a whole is wearable and portable. Passive linking member 29, compliant linking member 31, and actuating linking member 32 link movable body 25 to base body 26 by means of revolute joints 30a-30f, which each have an axis that is normal to the plane of the figure. Revolute joints 30a-30f provide for rotational coupling. For example, movable body 25 is rotationally coupled to passive linking member 29, compliant linking member 31, and actuating linking member 32. Passive linking member 29, compliant linking member 31, and actuating linking member 32 are rotationally coupled to base body 26.

Actuating element 27 of actuating linking member 32 is coupled to base body 26 at revolute joint 30a and is coupled to movable body 25 at revolute joint 30b. Actuating linking member 32 couples base body 26 to movable body 25 at revolute joints 30a and 30b. Revolute joint 30a is disposed in a fixed position on base body 26. Compliant element 28 of compliant linking member 31 is coupled to base body 26 at revolute joint 30c and is coupled to movable body 25 at revolute joint 30d. Thus, compliant linking member 31 couples base body 26 to movable body 25 at revolute joints 30c and 30d. Revolute joint 30c is disposed in a fixed position on base body 26. Movable body 25 is also coupled to base body 26 by passive linking member 29. Passive linking member 29 is coupled to movable body 25 at revolute joint 30e and is coupled to base body 26 at revolute joint 30f. Revolute joint 30f is disposed in a fixed position on base body 26.

Therefore, compliant element 28 and actuating element 27 are disposed in parallel between movable body 25 and base body 26 to form active compliant parallel device 900. As compliant element 28 compresses or extends, compliant linking member 31 changes in length. The change in length of compliant linking member 31 produces a force which pushes or pulls on movable body 25 at revolute joint 30d, causing movable body 25 to move with respect to base body 26. Similarly, actuating element 27 pushes or pulls on movable body 25 at revolute joint 30b by lengthening or shortening actuating linking member 32, causing movable body 25 to move with respect to base body 26. Passive linking member 29 is coupled to movable body 25 such that as movable body 25 moves, passive linking member 29 also moves. Passive linking member 29 rotates about revolute joint 30f as actuating element 27 and compliant element 28 act on movable body 25. The rotation or motion of passive linking member 29 is thereby controlled through movable body 25 by compliant element 28 and actuating element 27.

Figure 9B:
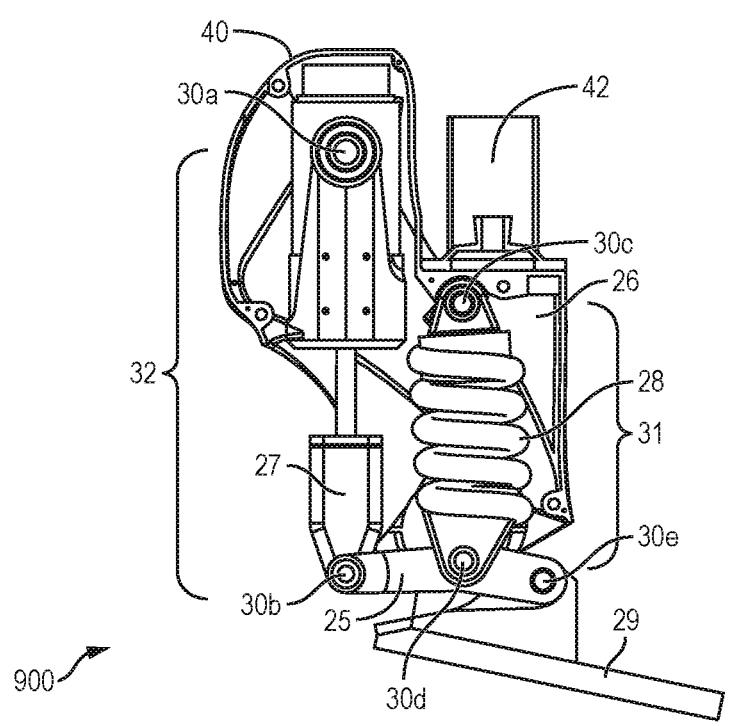

FIG. 9b shows a cutaway view of active compliant parallel device 900, which is depicted schematically in FIG. 9a. In FIG. 9b, active compliant parallel device 900 is implemented into an ankle joint of a below the knee prosthesis, which is also commonly known as a foot-ankle prosthesis. Active compliant parallel device 900 constitutes a robotic joint or a prosthetic joint, such as an ankle joint, knee joint, or other joint. Active compliant parallel device 900 includes compliant element 28 and actuating element 27 disposed in parallel to control the movement of movable body 25 and passive linking member 29. Passive linking member 29 is the end effector, or working element, of active compliant parallel device 900. Passive linking member 29 represents the foot in the foot-ankle prosthesis shown in FIG. 9b.

Compliant element 28 may be a tuned helical or coil spring with a stiffness which is optimized for efficient storage and release of energy during gait. Actuating element 27 may be a direct current (DC) motor with a gear ratio optimized for efficient use of power during actuation. Actuating element 27 and compliant element 28 work in parallel to mimic the action of the muscles, tendons, ligaments, and joints at work in a human ankle. Actuating element 27 and compliant element 28 are contained in a housing 40 of the foot-ankle prosthesis. Shank 42 or housing 40 of the foot-ankle prosthesis includes or couples to a socket, which fits onto a residual limb of the user. The user inputs forces through shank 42 acting on active compliant parallel device 900. Housing 40 and shank 42 are fixed with respect to base body 26 and comprise part of base body 126. Base body 26 encompasses the portions of active compliant parallel device 900 which are fixed together within the device.

FIGS. 10a-10e show an active compliant parallel mechanism incorporated into a lower leg, or foot-ankle, prosthesis during the different phases of human gait. Gait is a cyclical pattern of leg and foot movement that creates locomotion. A gait cycle is defined for a single leg and begins with the initial contact of the foot with the ground or heel strike. The conclusion of a gait cycle occurs when the same foot makes a second heel strike. The gait cycle can be divided into two phases, stance phase and swing phase. Stance phase begins with heel strike and ends when the toe of the same foot leaves the ground. Swing phase begins when the foot leaves contact with the ground and ends with heel strike of the same foot.

During a typical walking gait cycle, the moment required from a human reaches a maximum value of approximately 1.25 newton meters per kilogram (N-m/kg) of body weight, while the typical velocity reaches a maximum of approximately 450 degrees per second, and the maximum power reaches approximately 6.5 watts per kilogram (W/kg) of body weight. Thus, the output moment, for example, ranges from about 1-1.5 N-m/kg of body weight. The output velocity ranges from about 400-450 degrees per second. The output power ranges from about 6-7 W/kg of body weight. Through the use of active compliant parallel device 900, approximately the same output moment, velocity, and power required during gait is supplied from an actuator which provides 2.3 W/kg of body mass.

Figure 10A:
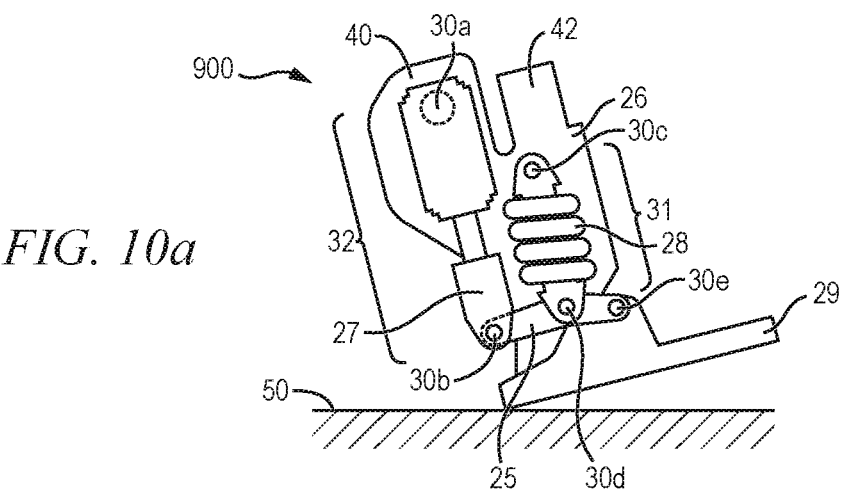
FIGS. 10a-10e illustrate an active compliant parallel device during the phases of human gait.

FIG. 10a shows active compliant parallel device 900 incorporated into a foot-ankle prosthetic device shown during the heel strike phase of a human gait step. During heel strike, passive linking member 29 makes contact with ground 50. A portion of passive linking member 29 representing the heel of the foot contacts ground 50 and passive linking member 29 begins to rotate downward, or in the direction of plantar flexion, toward ground 50. Compliant element 28 begins to extend as passive linking member 29 rotates toward ground 50. As compliant element 28 extends and passive linking member 29 rotates, the position of movable body 25 changes. The relative positions of movable body 25, passive linking member 29, compliant linking member 31, and actuating linking member 32 change throughout the gait cycle. The change in geometry within active compliant parallel device 900 changes the torque required from actuating element 27. In one embodiment, actuating element 27 is inactive during the heel strike phase of the gait cycle. Alternatively, actuating element 27 engages during heel strike to add control or to help position active compliant parallel device 900.

Compliant linking member 31 and actuating linking member 32 each comprise a prismatic joint. The length of compliant linking member 31 is the distance between revolute joint 30c and revolute joint 30d. The length of compliant linking member 31 is determined by compression or extension of compliant element 28 and is related to the force applied to compliant element 28. The length of actuating linking member 32 is the distance between revolute joint 30a and revolute joint 30b. The length of actuating linking member 32 is controlled by actuating element 27. The length of compliant linking member 31 and actuating linking member 32 comprise the input positions for active compliant parallel device 900. Active compliant parallel device 900 is a kinematically redundant system, which includes a greater number of input position variables than output position variables. The output force of active compliant parallel device 900 is a function of the input force and the input position of each linking member.

The input and output positions of active compliant parallel device 900 are determined by measuring the length of compliant linking member 31 and actuating linking member 32 either directly or indirectly. In one embodiment, actuating element 27 is a screw-type motor and is encoded to count the number of rotations of the motor to calculate the length of actuating linking member 32. The length of compliant linking member 31 is determined indirectly by measuring the rotation at revolute joint 30f and by calculating the length of compliant linking member 31 using the length of actuating linking member 32 and the rotation at revolute joint 30f. Alternatively, sensors are disposed on one or more joints or linking members of active compliant parallel device 900 to measure the input positions of compliant linking member 31 and actuating linking member 32. In an implementation of active compliant parallel device 900 for an orthotic device, sensors may be disposed on a limb of the user and on the device. The input positions of active compliant parallel device 900 are denoted by variables (1).

$$x = [x_1, x_2]^T \qquad (1)$$

where: $x_1$ is the length of actuating linking member 32
$x_2$ is the length of compliant linking member 31

Alternatively, active compliant parallel device 900 includes one or more additional compliant members, linking members, damping members, or passive members coupled to base body 26 and movable body 25. The input positions of an alternative active compliant parallel mechanism including additional linking members are denoted by variables (2).

$$x = [x_1, x_2, x_3 \ldots]^T \qquad (2)$$

The output position of active compliant parallel device 900 is measured using a sensor disposed on revolute joint 30f to measure the rotation or angle of passive linking member 29. Alternatively, the output position may be measured directly or indirectly by sensors disposed on one or more joints or linking members of active compliant parallel device 900. The output position of passive linking member 29 in active compliant parallel device 900 is denoted as y.

Alternatively, active compliant parallel device 900 includes one or more additional linking members as outputs. The output positions of an alternative active compliant parallel mechanism including additional outputs are denoted by variables (3).

$$y = [y_1, y_2, y_3 \ldots]^T \qquad (3)$$

The output position, y, of active compliant parallel device 900 is a function of the input positions, $x_1$ and $x_2$. Alternatively, active compliant parallel device 900 includes one or more additional inputs or outputs. For an alternative active compliant parallel mechanism including additional inputs and outputs, the output position is written as a function of the input positions in equation (4).

$$y = [y_1(x_1, x_2, \ldots)\ y_2(x_1, x_2, \ldots)\ y_3(x_1, x_2, \ldots) \ldots]^T \qquad (4)$$

The velocity at the output is written as a function of the velocity of the inputs by taking the time derivative of the input and output positions, resulting in a matrix known as the Jacobian denoted by J in equation (5) and equation (6).

$$\dot{y} = J\dot{x} \qquad (5)$$

$$J = \begin{bmatrix} \frac{\partial y_1}{\partial x_1} & \frac{\partial y_1}{\partial x_2} & \frac{\partial y_1}{\partial x_n} \\ \frac{\partial y_2}{\partial x_1} & \ldots & \ldots \\ \frac{\partial y_m}{\partial x_1} & \ldots & \frac{\partial y_m}{\partial x_n} \end{bmatrix}, n > m \qquad (6)$$

For a kinematically redundant system such as active compliant parallel device 900, the number of inputs, represented by n, is greater than the number of outputs, represented by m. In one embodiment, active compliant parallel device 900 has one extra degree of freedom at the input. The extra degree of freedom allows the internal geometry of active compliant parallel device 900 to be controlled and the transmission ratio of actuating element 27 to be adjusted. In another embodiment, active compliant parallel device 900 has additional degrees of freedom to make a biarticular device. For example, active compliant parallel device 900 moves in the sagittal plane and in the coronal plane such that the device includes two directions of motion, or two degrees of freedom.

The power input into active compliant parallel device 900 equals the power output and is shown generally by equation (7).

$$\text{Power}_{in} = \dot{x}^T F_x = \dot{y}^T F_y = \text{Power}_{out} \quad (7)$$

where: $F_x$ is the input force or moment measured at the inputs
$F_y$ is the output force or moment of the end effector
$\dot{x}^T$ is the input velocity
$\dot{y}^T$ is the output velocity Applying equation (7) specifically with respect to active compliant parallel device 900, the input force, $F_x$, represents the force along actuating linking member 32 at length or position $x_1$ and the force along compliant linking member 31 at length or position $x_2$. The output force, $F_y$, represents the moment around revolute joint 30f, which is the joint about which passive linking member 29 rotates. The power output of active compliant parallel device 900 is equal to the sum of the power input from compliant element 28 and actuating element 27. The relationship between the input force of active compliant parallel device 900 and the output force is defined by equation (8). Equation (8) is obtained by substituting equation (5) into equation (7).

$$F_x = J^T F_y \quad (8)$$

The input positions of compliant linking member 31, actuating linking member 32, and passive linking member 29 vary with the amount of force put into the device by the user. As the user applies force to active compliant parallel device 900 during gait, compliant element 28 changes in length, which changes the ratio of input force to output force. Equation (5), the Jacobian, is highly dependent on the length of compliant linking member 31, i.e., the length of the spring, and is less dependent on the output angle of passive linking member 29. The geometry within active compliant parallel device 900, such as the position of each of revolute joints 30a-30f with respect to the linking members and base body 26, is selected to optimize the transmission ratio of the device. The stiffness of active compliant parallel device 900 is thereby is tuned by selecting the internal geometry of active compliant parallel device 900 according to the user's needs and desired stiffness of the device.

Active compliant parallel device 900 better mimics a human ankle over a range of activities. The anatomy and mechanical properties of the human ankle are such that the elasticity and the load displacement response of the ankle behave like a non-linear spring. Active compliant parallel device 900 has an adjustable or tunable stiffness to allow for high performance over a range of speeds. For example, as more force is applied to compliant element 28 and actuating element 27, the geometry of active compliant parallel device 900 changes so that less torque and more velocity is required from actuating element 27. When output force is high, active compliant parallel device 900 requires less torque and more velocity. When output torque is low, active compliant parallel device 900 requires more torque and less velocity.

Figure 10B:
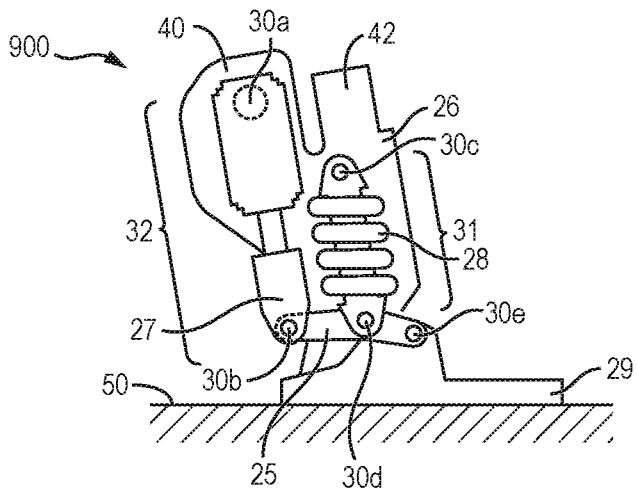

FIG. 10b shows active compliant parallel device 900 during the phase of a step where the foot is planted flat on the ground. In a human ankle, the foot rotates until planted flat on the ground. Within active compliant parallel device 900, passive linking member 29 behaves similarly to the human foot during plantar flexion. Passive linking member 29 rotates in the direction of plantar flexion with respect to active compliant parallel device 900 until passive linking member 29 is planted flat on ground 50. As passive linking member 29 rotates toward ground 50, compliant element 28 extends and compliant linking member 31 lengthens. Compliant element 28 acts to support the weight of the user and soften the impact on the user as passive linking member 29 contacts ground 50. Approximately zero or negligible power is required from actuating element 27 during the phase of gait where the foot, passive linking member 29, is initially planted on ground 50.

Between the heel strike and foot planted phase of gait, passive linking member (prosthetic foot) 29 rotates with respect to base body 26 at joint 30f, which is hidden from view in FIGS. 10a-10e, but is shown schematically in FIG. 9a. Passive linking member 29 also rotates the direction of plantar flexion with respect to movable body 25 at joint 30e. The user provides energy inputted at shank 42 to rotate passive linking member 29 toward ground 50. The torque required from actuating member 27 is negligible as passive linking member 29 rotates toward ground 50.

Figure 10C:
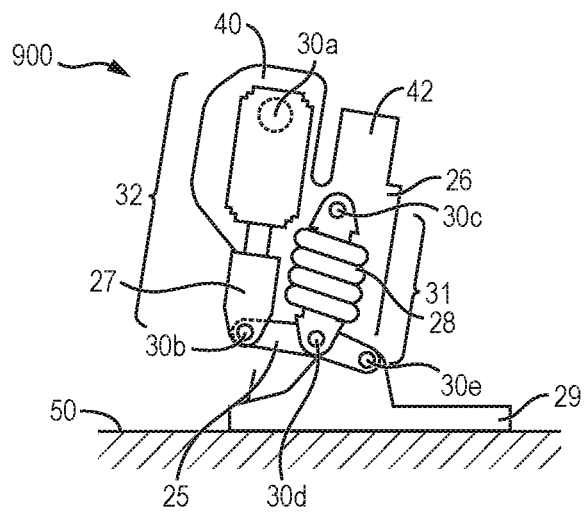

FIG. 10c shows active compliant parallel device 900 during the phase of a step where the shank moves over the foot, while the foot is planted flat on the ground. In a human ankle, the tibia moves over the ankle while the foot is planted on the ground. Within active compliant parallel device 900, shank 42 is controlled by the user to move shank 42, base body 26, and movable body 25 relative to passive linking member 29. The user inputs force on base body 26 at shank 42. Passive linking member 29 remains planted flat on ground 50 as the user forces base body 26 to move forward over passive linking member 29. Revolute joints 30a and 30c are fixed in position on base body 26. Base body 26 moves forward causing movable body 25 to change position with respect to passive linking member 29. As base body 26 moves forward over passive linking member 29, compliant element 28 within active compliant parallel device 900 changes from the slightly extended position from FIG. 10b to a compressed position in FIG. 10c. As a result of the compression of compliant element 28, the length of compliant linking member 31 shortens.

Compliant element 28 includes a spring, which is able to store and release energy. Compliant element 28 is compressed by the forward motion of base body 26 and stores potential energy during compression. The stiffness of compliant element 28 is selected to provide the optimal resistance to the user without causing too much resistance so as to cause the user to expend extra metabolic energy during gait. Actuating element 27 engages to compress compliant element 28. In one embodiment, actuating element 27 pulls on movable body 25 at revolute joint 30b to compress compliant element 28. The input position, velocity, or force of actuating element 27 is measured using a sensor. Based on the input measurement, actuating element 27 engages to change the length of actuating linking member 32, which causes a change to the internal geometry of active compliant parallel device 900. The change in geometry also causes a change in the length of compliant element 28 and compliant linking member 31. By changing the length of compliant element 28 by further compressing the spring, the additional energy is added by actuating element 27 and stored in compliant element 28.

Actuating element 27 engages as compliant element 28 is compressed to further compress compliant element 28.

Actuating element 27 engages to either shorten or lengthen actuating linking member 32, as needed to compress compliant element 28. The force on movable body 25 by actuating element 27 causes additional compression in compliant element 28. Compliant element 28 is compressed by the motion of base body 26 caused by the movement of shank 42 over passive linking member 29, and compliant element 28 is further compressed by the added power from actuating element 27. Actuating element 27 therefore, increases the amount of potential energy stored by compliant element 28. The potential energy stored in compliant element 28 is later used during the push-off phase of the gait cycle.

A traditional passive device using only a spring is able to store the amount of energy inputted by the user. The energy returned to the user in a traditional passive device is equal to the energy put into the spring compression by the user. Active compliant parallel device 900 allows the spring, compliant element 28, to store additional energy by increasing the spring compression using a motor, actuating element 27. The energy returned to the user by active compliant parallel device 900 is greater than the energy put in by the user.

Figure 10D:
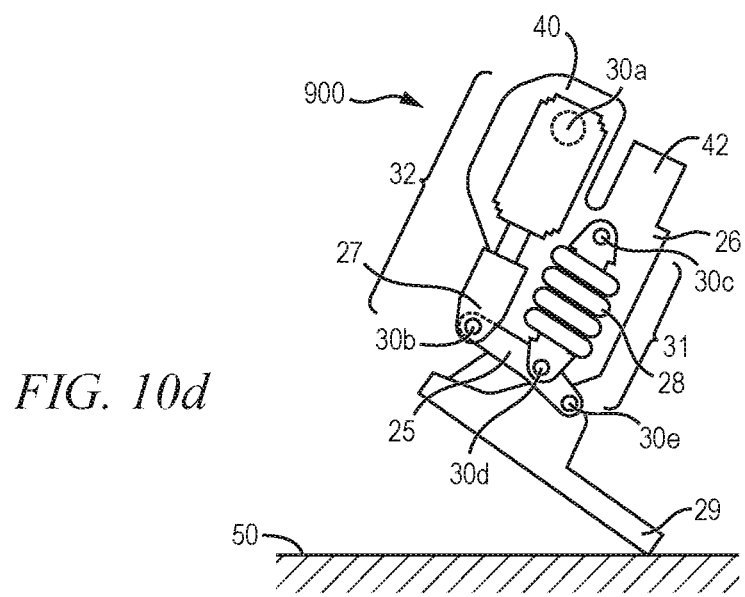

FIG. 10d shows active compliant parallel device 900 during the push off phase of a gait step. During push off, the human ankle behaves approximately like a linear spring as the foot plantar flexes and pushes into the ground and the heel is raised. Compliant element 28 and actuating element 27 of active compliant parallel device 900 provide a combined power output to mimic the push off phase of the gait cycle.

The potential energy stored in compliant element 28 during the phase of gait shown in FIG. 10c is released as kinetic energy during the push-off phase shown in FIG. 10d. Compliant element 28 extends from the compressed position to force movable body 25 at revolute joint 30d downward with respect to base body 26. Actuating element 27 pulls on movable body 25 at revolute joint 30b to shorten actuating linking member 32 and to change the position of movable body 25. Therefore, the output of both compliant element 28 and actuating element 27 causes the movement of movable body 25 and passive linking member 29. Passive linking member 29, which is coupled to movable body 25 at revolute joint 30e, rotates in a plantar flexion direction with respect to base body 26. The movement of passive linking member 29 mimics the plantar flexion motion of a foot during push off. The rotation of passive linking member 29 causes the lower leg prosthetic device with active compliant parallel device 900 to move into the push off phase of gait.

The push off phase of gait requires the maximum amount of power compared to the other phases of gait. For example, an 80 kg human may require up to 350 W of peak power in the ankle during push off. The amount of energy output provided by active compliant parallel device 900 during push off is equal to the sum of the power provided by actuating element 27 and compliant element 28. Compliant element 28 provides power as the spring unloads from the compressed position. The amount of power provided by compliant element 28 is directly related to the amount of compression in the spring. Actuating element 27 provides power by pulling on movable body 25 at revolute joint 30b during push off. Actuating element 27 requires peak power during the push off phase. The combined power of compliant element 28 and actuating element 27 results in the output power for active compliant parallel device 900.

The peak power output required from actuating element 27 is reduced in active compliant parallel device 900 compared to other power prosthesis designs. The parallel design of active compliant parallel device 900 allows actuating element 27 to supply power to the device over a longer time interval. Actuating element 27 begins supplying power to compress compliant element 28 during the previous phase of gait shown in FIG. 10c. The additional energy added to compliant element 28 is stored by compliant element 28 until the push off phase of gait. When compliant element 28 extends or unloads at push off, the power output of compliant element 28 contributes to push off and less power is required from actuating element 27 during push off. Instead of supplying all of the power needed for push off at the time of push off, some power is supplied earlier by actuating element 27 and is stored in compliant element 28. Actuating element 27 supplies some power to compress compliant element 28 prior to push off, and compliant element 28 stores the energy from actuating element 27 until push off. The energy stored in compliant element 28 is released during push off as the spring extends thereby contributing power to push off. Actuating element 27 continues to supply power during push off. Therefore, actuating element 27 engages over a time interval that is longer than the push off phase of gait and results in a lower peak power requirement during push off. The energy contributed by compliant element 28 at push off results in less peak power required from actuating element 27 while the overall power output of active compliant parallel device 900 remains high.

The peak power output required from actuating element 27 determines the size of the motor required for actuating element 27 to perform push off. A greater peak power requirement means a larger motor is needed to supply that peak power. Active compliant parallel device 900 reduces the peak power output required from actuating element 27 during push off. Therefore, the size of the motor used for actuating element 27 is smaller. In one embodiment, actuating element 27 is a 150 W DC motor with a 28 volt battery. A smaller motor allows for a more compact and lighter weight prosthetic device, which is more comfortable for the user to wear.

The peak power output of active compliant parallel device 900 is also greater than the peak power output of a simple lever motor or passive spring. Actuating element 27 supplies more power during a gait cycle than is needed at the output (during push off), by storing energy in the spring over a relatively long time period (prior to push off) and subsequently releasing that energy over a relatively short time period (during push off). The increase in energy return by active compliant parallel device 900 results in improved device performance over other active or passive prostheses. Active compliant parallel device 900 returns a greater amount of energy during push off than the amount of energy put in by the user. The improved power output of the device results in less metabolic energy being required by the user to maintain a normal gait.

Figure 10E:
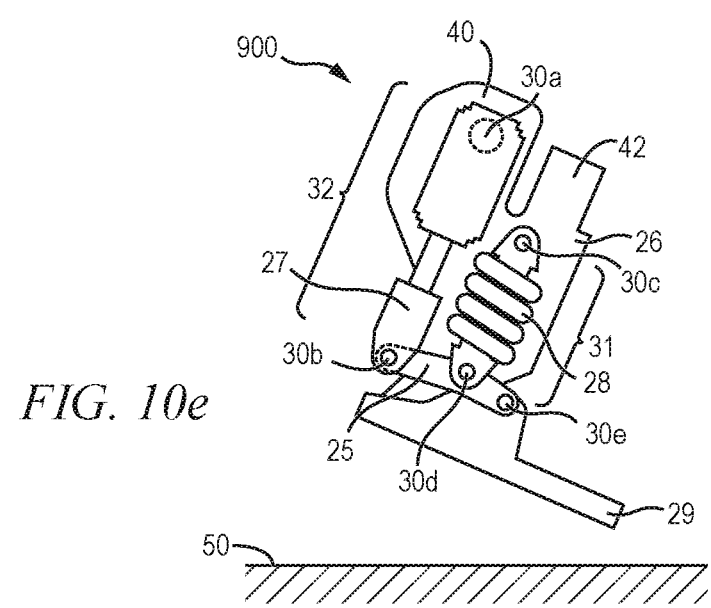

FIG. 10e shows active compliant parallel device 900 during the swing through phase of a gait step. The human ankle returns to a neutral position during swing phase, when the foot is off the ground. Similarly, the prosthetic device incorporating active compliant parallel device 900 returns to a neutral position during swing phase. Passive linking member 29 moves in the direction of dorsiflexion as the device returns to a neutral position. Actuating element 27 requires negligible or low power as actuating element 27 returns to a position ready for the next gait cycle. Compliant element 28 returns to a neutral, uncompressed and non-extended position.

Figure 11:
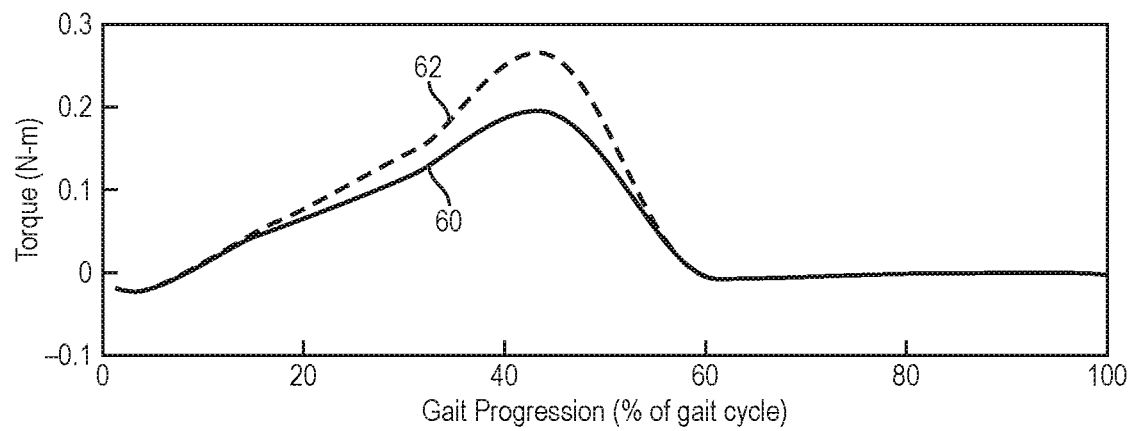
FIG. 11 illustrates a graph showing peak torque required for the active compliant parallel device during the phases of human gait.

FIG. 11 compares the torque required from active compliant parallel device 900 to the torque required from a lever motor used in a non-parallel, powered prosthetic device during a single gait cycle. Active compliant parallel device 900 combines compliant element 28, a spring, with actuating element 27 a motor, to store and release energy during gait. The torque required by actuating element 27 of active compliant parallel device 900 during a gait cycle is shown as line 60. The torque required by a powered lever motor within an ankle prosthesis during a gait cycle is shown as line 62. The peak torque required from a motor during a gait cycle occurs at the push off phase, which is shown at approximately 45-50% of the gait progression along the x-axis of FIG. 11. Active compliant parallel device 900, shown at line 60, requires approximately 0.195 N-m of torque at push off. A lever motor, shown at line 62, requires over 0.25 N-m of torque at push off. Therefore, the lever motor without a parallel mechanism requires more torque during push off than active compliant parallel device 900. Active compliant parallel device 900 reduces the torque required by the motor by 26% during a normal walking gait.

The efficiency of a DC motor is highly dependent on the motor torque. A lower peak torque requirement results in a lower peak power use by actuating element 27. A smaller motor is used for actuating element 27 because active compliant parallel device 900 has a lower peak power requirement. The more efficient energy usage also allows actuating element 27 i.e. the motor, to run cooler and allow for longer operation. Overall, the lower peak torque in active compliant parallel device 900 results in a higher performance prosthesis.

Figure 12:
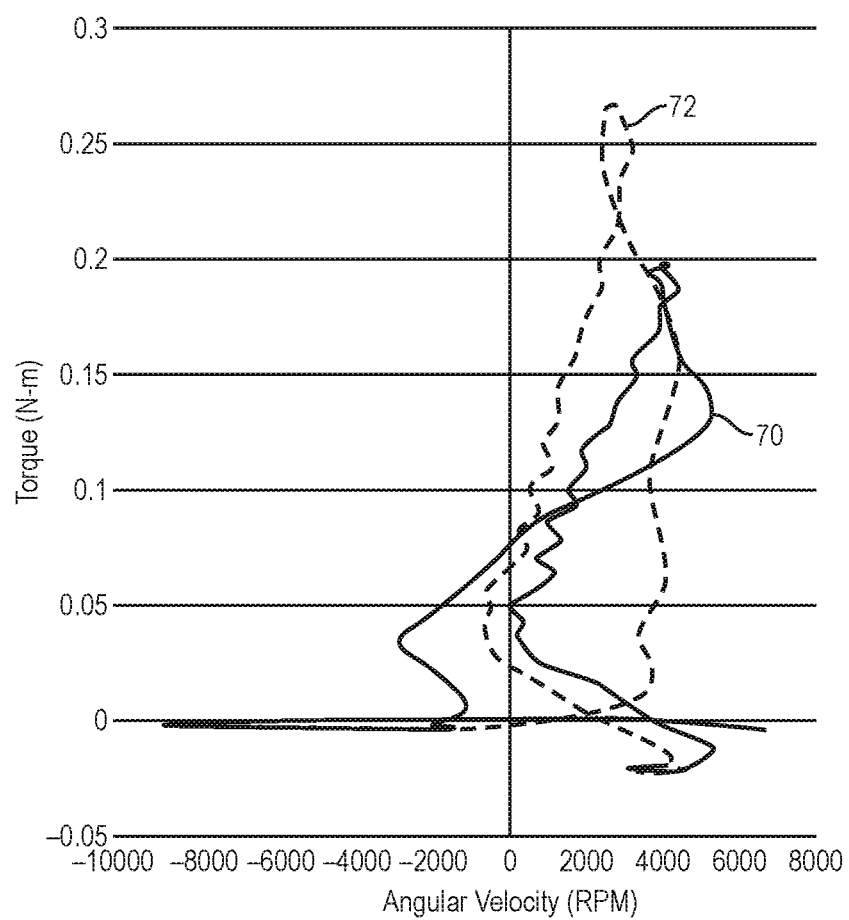
FIG. 12 illustrates a graph showing torque required for the active compliant parallel device related to angular velocity.

FIG. 12 compares the torque required from the active compliant parallel device 900 to the torque required from an active compliant series mechanism used in a prosthetic device during a single gait cycle. The angular velocity and torque at the motor for each device is shown. The comparison in FIG. 12 assumes a motor, or actuating element 27 having a 1 millimeter (mm) pitch screw as a rotary to linear transmission and an 80 kg subject walking with a step frequency of 1.25 seconds per step.

Active compliant parallel device 900 includes actuating element 27 and compliant element 28 disposed in parallel. The torque required from actuating element 27 of active compliant parallel device 900 is shown as line 70. Active compliant parallel device 900, shown at line 70 requires approximately 0.195 N-m of torque at push off.

An active compliant series mechanism differs from active compliant parallel device 900 in that the spring and motor are disposed in series between a base body and a movable body. The torque required by the motor in a series mechanism is shown at line 72. An active compliant series mechanism, shown as line 72, requires approximately 0.266 N-m of torque at push off. The peak torque of active compliant parallel device 900, at line 70, is lower than the peak torque of the series mechanism, at line 72. A similar angular velocity is achieved by active compliant parallel device 900 as is achieved by the series mechanism. Therefore, active compliant parallel device 900 achieves a similar velocity as the series mechanism, but requires less peak torque to reach that similar velocity. A smaller motor is used for active compliant parallel device 900 than is used for the series mechanism to achieve a similar gait speed. Active compliant parallel device 900 is lighter in weight than current devices and provides greater power and improved gait performance.

Efficiency of a DC motor is less dependent on the angular velocity of the motor, and is much more dependent on motor torque. Further, a DC motor operates at peak efficiency over a relatively narrow window of torque. The lower peak torque requirement from actuating element 27 of active compliant parallel device 900 results in more efficient operation of actuating element 27 and results in a higher performance prosthesis. Actuating element 27 operates within more favorable torque and velocity zones compared to a direct drive system. Therefore, the DC motor operates closer to peak efficiency. An average efficiency of actuating element 27 is approximately 80% within active compliant parallel device 900 because actuating element 27 operates closer to the optimal operating velocity and torque. Active compliant parallel device 900 also provides greater impulse tolerance and increased force fidelity over direct drive systems. Increasing the efficiency of actuating element 27 also improves the overall efficiency of active compliant parallel device 900.

Active compliant parallel device 900 is employed in a variety of applications. Some application examples include fields that require actuation of joints for locomotion, necessitate high force and speed from lightweight devices, require actuation of arms, hands, legs, or feet, and fields using devices that have robotic end effectors which interact with unstructured or unpredictable environments. In addition, the devices may be utilized in any field where the storing and releasing of potential energy in a compliant component, such as a spring, is necessary.

Figure 13:
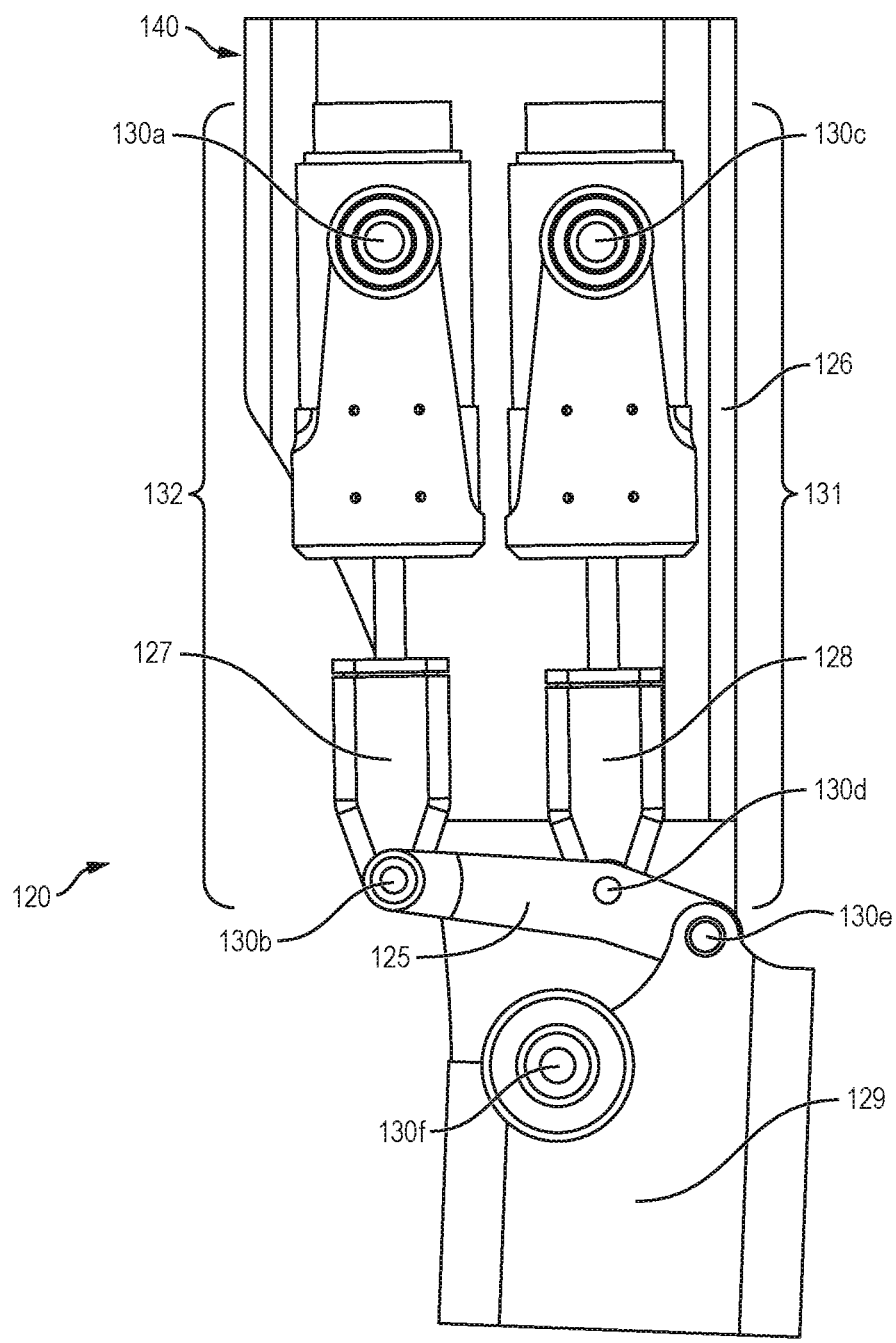
FIG. 13 illustrates another embodiment of a lower limb prosthetic device including a parallel actuator device.

FIG. 13 shows another embodiment of a lower limb prosthetic device including a parallel actuator device. The parallel actuator device 120 is a parallel mechanism including two actuating elements in parallel to actuate a movable portion. In one embodiment, parallel actuator device 120 is implemented into a prosthetic hip or prosthetic knee device. Parallel actuator device 120 constitutes a robotic joint or a prosthetic joint, such as a knee joint, hip joint, or other joint. Parallel actuator device 120 includes actuating element 127 and actuating element 128 disposed in parallel to control the movement of movable body 125 and passive linking member 129. Passive linking member 129 is the end effector, or working element, of parallel actuator device 120. Passive linking member 129 represents a lower leg in a knee prosthesis or an upper leg in a hip prosthesis. A prosthetic hip or prosthetic knee device also includes an artificial limb extending from passive linking member 129 down to ground. For example, active compliant parallel device 900 is coupled to the distal end of parallel actuator device 120 to provide a complete knee-ankle-foot prosthesis. Alternatively, a passive device or additional passive linking members are coupled to a distal end of parallel actuator device 120. A plurality of parallel actuator devices 120 or active compliant parallel devices 900 can be coupled together to form a multi-joint prosthesis.

Movable body 125 is linked to base body 126 by passive linking member 129, actuating linking member 131, and actuating linking member 132. Actuating linking members 131 and 132 are disposed in parallel between movable body 125 and base body 126. Actuating linking members 131 and 132, movable body 125, base body 126, and passive linking member 129 constitute the parallel mechanism of parallel actuator device 120. Actuating linking member 132 includes actuating element 127, which can be a controllable position actuator or a force type actuator, such as an electric motor and lead screw or ball screw, hydraulic, pneumatic, direct-drive, series-elastic, electroactive polymer-based, chemical-based, or other actuation scheme. Actuating linking member 131 includes actuating element 128, which can also be a controllable position actuator or a force type actuator, such as an electric motor and lead screw or ball screw, hydraulic, pneumatic, direct-drive, series-elastic, electroactive polymer-based, chemical-based, or other actuation scheme.

Base body 126 is the fixed portion of parallel actuator device 120 to which the movable members are attached. Base body 126 is fixed with respect to the user, while the device as a whole is wearable and portable. Passive linking member 129 and actuating linking members 131 and 132 link movable body 125 to base body 126 by means of joints or revolute joints 130a-130f, which each have an axis that is normal to the plane of the figure. Revolute joints 130a-130f provide for rotational coupling. For example, movable body 125 is rotationally coupled to passive linking member 129 and to actuating linking members 131 and 132. Passive linking member 129 and actuating linking members 131 and 132 are rotationally coupled to base body 126. Alternatively, joints 130a-130f are prismatic joints, screw-type joints, or another joint type.

Actuating element 127 of actuating linking member 132 is coupled to base body 126 at revolute joint 130a and is coupled to movable body 125 at revolute joint 130b. Actuating linking member 132 couples base body 126 to movable body 125 at revolute joints 131a and 131b. Revolute joint 131a is disposed in a fixed position on base body 126. Actuating element 128 of actuating linking member 131 is coupled to base body 126 at revolute joint 130c and is coupled to movable body 125 at revolute joint 130d. Thus, actuating linking member 131 couples base body 126 to movable body 125 at revolute joints 130c and 130d. Revolute joint 130c is disposed in a fixed position on base body 126. Movable body 125 is also coupled to base body 126 by passive linking member 129. Passive linking member 129 is coupled to movable body 125 at revolute joint 130e and is coupled to base body 126 at revolute joint 130f. Revolute joint 130f is disposed in a fixed position on base body 126.

Actuating elements 127 and 128 are DC motors with a gear ratio optimized for efficient use of power during actuation. Actuating elements 127 and 128 work in parallel to mimic the action of the muscles, tendons, and ligaments at work in a human hip or knee joint. Actuating elements 127 and 128 are contained in a housing 140 of the prosthetic device. Housing 140 of the knee or hip prosthesis includes a socket or couples to a socket, which fits onto a residual limb of the user. The user inputs forces through housing 140 acting on parallel actuator device 120. Housing 140 is fixed with respect to base body 126 and comprises part of base body 126. Base body 126 encompasses the portions of parallel actuator device 120 which are fixed together within the device.

Figure 14:
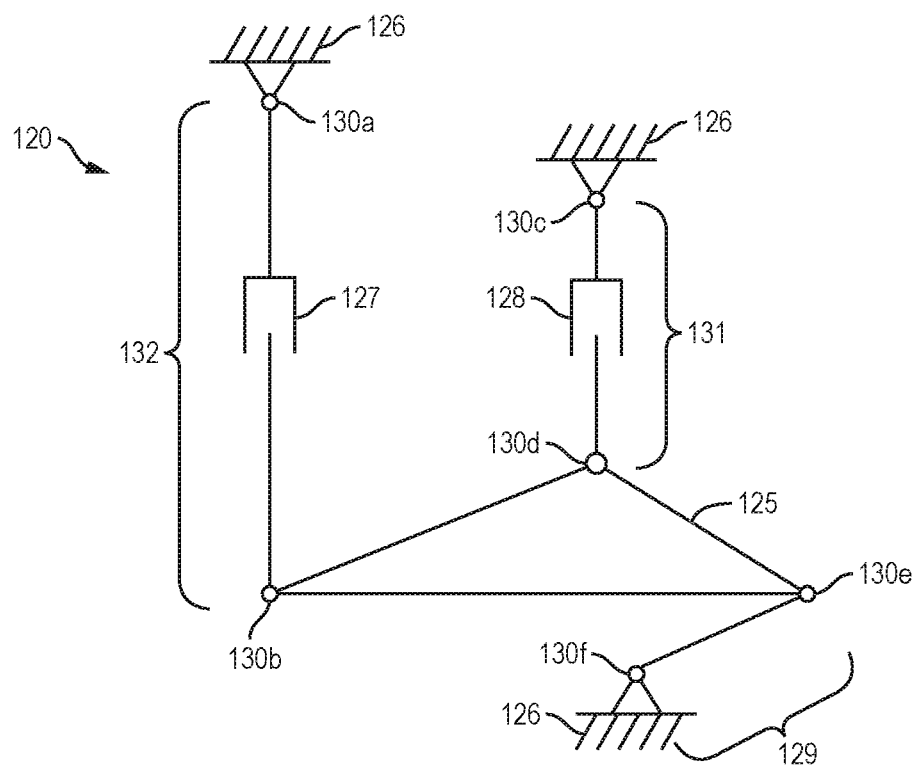
FIG. 14 illustrates a schematic representation of a parallel actuator device.

FIG. 14 shows a schematic representation of the parallel actuator device 120 from FIG. 13. Actuating elements 127 and 128 are disposed in parallel between movable body 125 and base body 126 to form parallel actuator device 120. As actuating elements 127 and 128 engage, actuating linking members 131 and 132 change in length. Actuating element 128 produces a force which pushes or pulls on movable body 125 at revolute joint 130d, causing movable body 125 to move with respect to base body 126. Similarly, actuating element 127 pushes or pulls on movable body 125 at revolute joint 130b by lengthening or shortening actuating linking member 132, causing movable body 125 to move with respect to base body 126. Passive linking member 129 is coupled to movable body 125 such that as movable body 125 moves, passive linking member 129 also moves. Passive linking member 129 rotates about revolute joint 130f as actuating elements 127 and 128 act on movable body 125. The rotation or motion of passive linking member 129 is thereby controlled through movable body 125 by actuating elements 127 and 128. Passive linking member 129, representing the leg, is the end effector or working element of parallel actuator device 120.

Parallel actuator device 120 is used to supplement or replace various joints within the human body. Parallel actuator device 120 is shown incorporated into a hip prosthesis. However, parallel actuator device 120 is also used in other lower leg prosthetic devices, such as the knee and ankle. Parallel actuator device 120 is also adaptable for upper body prosthetics, such as the shoulder, elbow, wrist, or fingers. As shown in FIGS. 1-8, additional degrees of freedom or constraints are added to parallel actuator device 120 to suit a particular performance need. In one example, a compliant element is added to parallel actuator device 120 to store and release energy. The compliant element is coupled between movable body 125 and passive linking member 129. Alternatively, the compliant element is coupled between passive linking member 129 and base body 126. In another example, a damper is added to parallel actuator device 120 to provide additional control to the device.

Figure 15A:
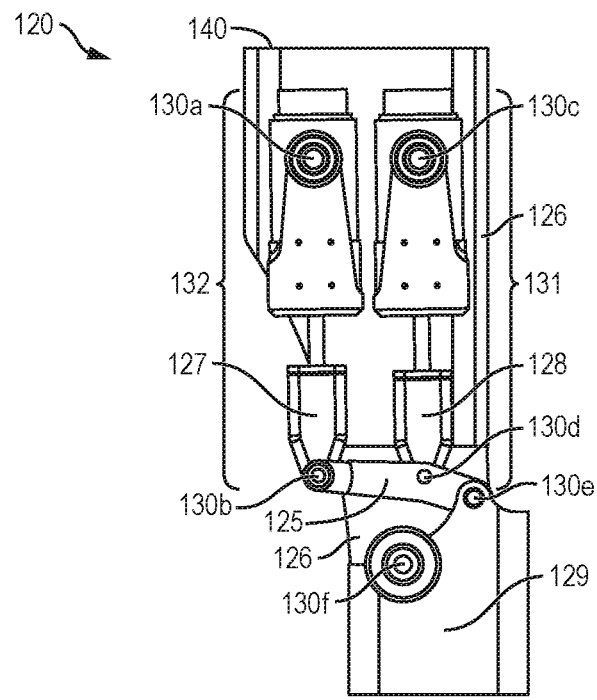
FIGS. 15a-15c illustrate a parallel actuator device during the phases of human gait.
Figure 15B:
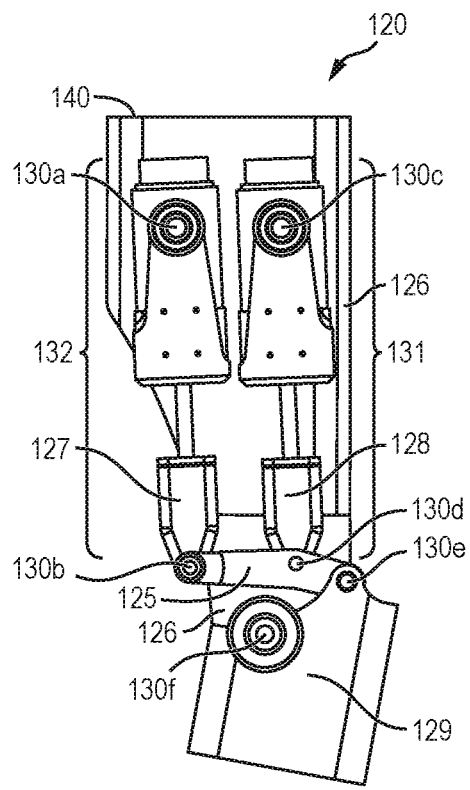
Figure 15C:
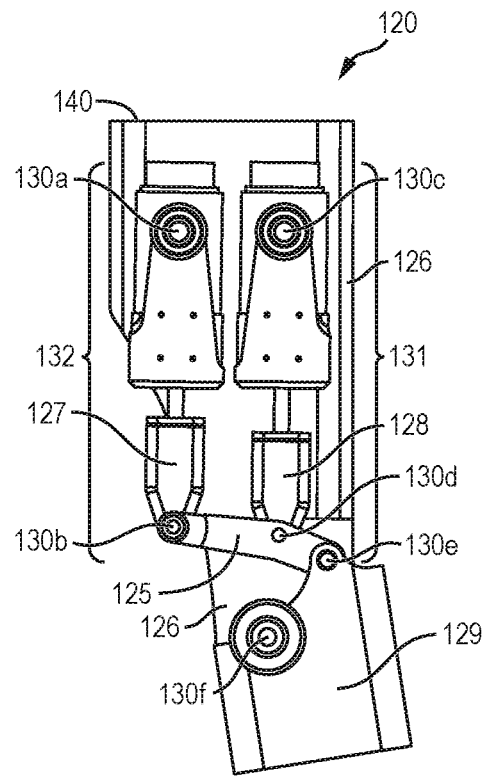

FIGS. 15a-15c show a parallel actuator device 120 incorporated into a hip prosthesis during the different phases of human gait. The phases of gait for a human hip can be divided into two phases, stance phase and swing phase, where the two phases are separated by heel strikes. Stance phase includes the duration of a step where the limb is in contact with the ground and the limb is bearing weight. Swing phase includes the duration of a step where the limb leaves contact with the ground, swings forward, and is ready for the next heel strike.

FIG. 15a shows a parallel actuator device 120 incorporated into a hip prosthesis during mid-stance phase of a human gait step. During stance phase for a human leg, the hip moves from a flexed position to an extended position, and reaches a neutral position at the mid-stance point. Parallel actuator device 120 mimics flexion and extension of the hip joint. Passive linking member 129 includes an extension portion, such as another active or passive artificial lower limb, which contacts the ground. During stance phase, parallel actuator device 120 engages to push passive linking member 129 in the posterior direction similar to the motion during hip extension as the user begins the push-off phase of gait. Actuating elements 127 and 128 work in parallel to move the limb as a quadricep muscle would move the leg.

To mimic the human quadricep muscle, the velocities of actuating elements 127 and 128 are selected to move movable body 125 and passive linking member 129. Actuating elements 127 and 128 are controlled by a system that determines the velocities of actuating elements 127 and 128 based on algorithms designed to match human movement. Actuating element 127 pulls on movable body 125 at revolute joint 130b, shortening actuating linking member 132, to change the position of movable body 125. Actuating element 128 pushes on movable body 125 at revolute joint 130d, lengthening actuating linking member 131, to assist actuating element 127 in moving movable body 125. The output of both actuating elements 127 and 128 causes the movement of movable body 125 and passive linking member 129. In one embodiment, actuating linking member 132 has a length that is greater than the length of actuating linking member 131. Parallel actuator device 120 requires a higher velocity from actuating element 127 in order to move movable body 125 than the velocity required from actuating element 128. Both actuating elements 127 and 128 engage in opposite directions to move passive linking member 129. For example, actuating element 127 pulls on movable body 125 and actuating element 128 pushes on movable body 125.

The velocity of actuating element 127 is higher than the velocity of actuating element 128 during stance phase. In one embodiment, actuating element 128 is inactive during stance phase, and actuating element 127 engages to pull movable body 125 and passive linking member 129 into position. In another embodiment, actuating element 128 engages to position actuating linking member 131 and movable body 125 in preparation for swing phase.

Passive linking member 129, which is coupled to movable body 125 at revolute joint 130e, rotates as actuating elements 127 and 128 engage to shorten actuating linking member 132 and to lengthen actuating linking member 131. Passive linking member 129 is rotationally affixed to base body 126 at revolute joint 130f. Passive linking member 129 moves in the posterior direction around revolute joint 130f with respect to base body 126. The posterior rotation of passive linking member 129 represents hip extension and the push off phase of gait.

FIG. 15b shows a parallel actuator device 120 incorporated into a hip prosthesis at the end of stance phase of a human gait step where the foot pushes off the ground. The hip joint is extended at the end of stance phase. Similarly, parallel actuator device 120 mimics hip extension where passive linking member 129 is rotated posteriorly with respect to base body 126. Actuating linking member 132 is shortened and actuating linking member 131 is lengthened. Actuating element 127 operates with high force and low velocity during stance phase. The force and velocity of actuating element 127 mimics the hip joint during stance. The hip joint has a high moment and low force during stance as muscles extend the hip joint in a slow, steady motion. Similarly, actuating elements 127 and 128 actuate to move passive linking member 129 in a slow, steady motion. Stance phase ends when the limb pushes off the ground, and parallel actuator device 120 moves into swing phase of the gait cycle.

FIG. 15c shows a parallel actuator device 120 incorporated into a hip prosthesis in swing phase of a human gait step. During swing phase, the hip joint flexes, swinging the leg forward until the foot strikes the ground. The moment at the hip joint is low and the velocity is high during swing phase. Similarly, parallel actuator device 120 operates with a high velocity to swing passive linking member 129 in the anterior direction. Actuating element 128 pulls on movable body 125 at revolute joint 130d, shortening actuating linking member 131, to change the position of movable body 125. Passive linking member 129 rotates at revolute joint 130f in an anterior direction with respect to base body 126. Actuating element 127 engages to position movable body 125 and to prepare for foot strike. Alternatively, actuating element 127 is inactive during the swing phase of the gait cycle. Generally, actuating linking member 132 lengthens as actuating element 127 engages during swing phase. Actuating element 127 operates with low force and high velocity during swing phase. The force and velocity of actuating element 127 mimics the hip joint during swing phase.

Actuating elements 127 and 128 acting in parallel on movable body 125 to move passive linking member 129 gives parallel actuator device 120 kinematic redundancy. Parallel actuator device 120 includes one revolute output degree of freedom and a kinematic redundancy rate of one. Kinematic redundancy refers to the number of degrees of freedom at the input in excess of the degrees of freedom at the output necessary to complete a given task. The extra degree of freedom for parallel actuator device 120 is achieved through the design layout of revolute joints 131a-130f, actuating linking members 131 and 132, movable body 125, and passive linking member 129. Therefore, parallel actuator device 120 constitutes a parallel kinematically redundant mechanism or device. Combining actuating elements 127 and 128 in parallel between base body 126 and movable body 125 allows parallel actuator device 120 to be designed with passive linking member 129 as the end effector or working element, rather than with movable body 125 as the end effector. The benefit of the parallel kinematically redundant design is that the desired output position of passive linking member 129 is achievable with many different combinations of input positions. Actuating elements 127 and 128 are used to change the internal geometry of parallel actuator device 120 without changing the output position of passive linking member 129. The result is that the output force and velocity for parallel actuator device 120 is less dependent upon the input position of the device. Parallel actuator device 120 performs with high velocity or with high force independent of the starting position for the device. The velocity of actuating elements 127 and 128 is selected to produce a force-velocity relationship that better mimics a human muscle than single actuator designs.

The input positions of parallel actuator device 120 are determined by measuring the length actuating linking members 131 and 132 either directly or indirectly. In one embodiment, actuating elements 127 and 128 are screw-type motors encoded to count the number of rotations of the motors and to calculate the length of actuating linking members 131 and 132. Alternatively, sensors are disposed on one or more joints or linking members of parallel actuator device 120 to measure the input positions of actuating linking members 131 and 132. In an implementation of parallel actuator device 120 for an orthotic device, sensors may be disposed on a limb of the user and on the device. The input positions of parallel actuator device 120 are denoted by variables (9).

$$x=[x_1, x_2]^T \quad (9)$$

where: $x_1$ is the length of actuating linking member 132
$x_2$ is the length of actuating linking member 131

Alternatively, parallel actuator device 120 includes one or more additional compliant members, linking members, damping members, or passive members coupled to base body 126 and movable body 125. The input positions of an alternative parallel actuator mechanism including additional linking members are denoted by variables (10).

$$x=[x_1, x_2, x_3 \ldots]^T \quad (10)$$

The output position of parallel actuator device 120 is measured using a sensor disposed on revolute joint 130f to measure the rotation or angle of passive linking member 129. Alternatively, the output position may be measured directly or indirectly by sensors disposed on one or more joints or linking members of parallel actuator device 120. The output position of passive linking member 129 in parallel actuator device 120 is denoted as y.

Alternatively, parallel actuator device 120 includes one or more additional linking members as outputs. For an alternative parallel actuator mechanism including additional outputs, the output positions may be the angle or length of an output joint and are denoted by variables (11).

$$y=[y_1, y_2, y_3 \ldots]^T \quad (11)$$

The output position, y, of parallel actuator device 120 is written as a function of the input positions, $x_1$ and $x_2$. Alternatively, parallel actuator device 120 includes one or more additional inputs or outputs. For an alternative parallel actuator mechanism including additional inputs and outputs, the output position is written as a function of the input positions generally in equation (12).

$$y=[y_1(x_1, x_2, \ldots) \; y_2(x_1, x_2, \ldots) \; y_3(x_1, x_2, \ldots) \ldots]^T \quad (12)$$

The output velocity is written as a function of the input velocity by taking the time derivative of the input and output positions, resulting in a matrix known as the Jacobian denoted by J in equation (13). The Jacobian is found by writing the function defining the output position of parallel actuator device 120 as a function of the input positions. The partial derivative of each output position is taken with respect to each input position.

$$J = \begin{bmatrix} \frac{\partial y_1}{\partial x_1} & \frac{\partial y_1}{\partial x_2} & \frac{\partial y_1}{\partial x_n} \\ \frac{\partial y_2}{\partial x_1} & \ldots & \ldots \\ \frac{\partial y_m}{\partial x_1} & \ldots & \frac{\partial y_m}{\partial x_n} \end{bmatrix}, \; n > m \quad (13)$$

For a kinematically redundant system such as parallel actuator device 120, the number of inputs, represented by n, is greater than the number of outputs, represented by m. In one embodiment, parallel actuator device 120 has one extra degree of freedom at the input. The extra degree of freedom allows the internal geometry of parallel actuator device 120 to be controlled and the transmission ratio of actuating elements 127 and 128 to be adjusted. In another embodiment, parallel actuator device 120 has an additional degree of freedom to make a biarticular device. For example, parallel actuator device 120 moves in the sagittal plane and in the coronal plane such that the device includes two directions of motion.

The input velocities of actuating elements 127 and 128 are related to the output velocity of parallel actuator device 120 by equation (14).

$$\dot{y} = J \begin{bmatrix} \dot{x}_1 \\ \dot{x}_2 \end{bmatrix} \quad (14)$$

where: $\dot{x}_1$ is the input velocity of actuating element 127
$\dot{x}_2$ is the input velocity of actuating element 128
$\dot{y}$ is the output velocity of passive linking member 129
The power input of actuating elements 127 and 128 equals the power output of parallel actuator device 120 and is shown with equation (15).

$$F_y \dot{y} = F_1 \dot{x}_1 + F_2 \dot{x}_2 \quad (15)$$

where: $F_1$ is the input force of actuating element 127
$F_2$ is the input force of actuating element 128
$F_y$ is the output force of passive linking member 129
Equation (14) and equation (15) are used to determine the force-velocity relationship of actuating elements 127 and 128 to calculate the output force-velocity relationship for parallel actuator device 120.

Figure 16:
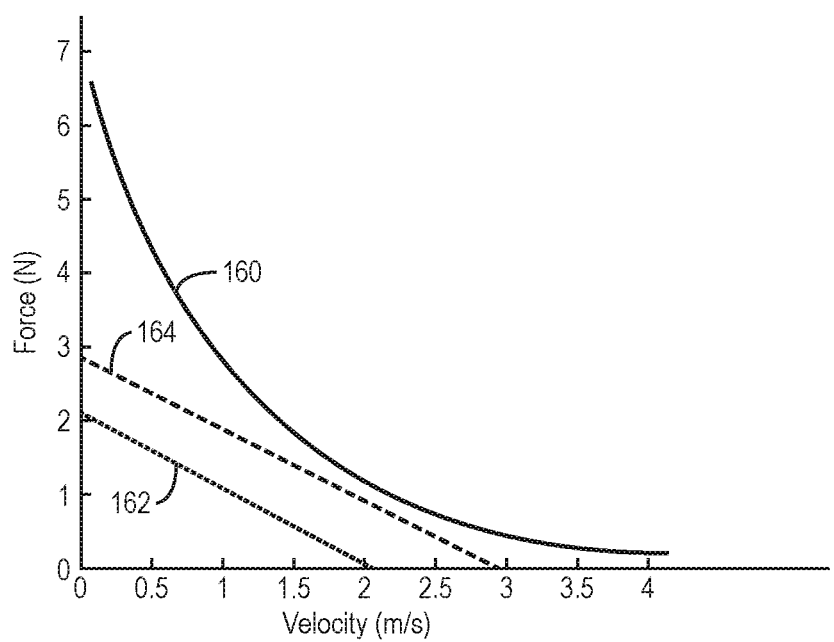
FIG. 16 illustrates a graph showing the force-velocity relationship of a parallel actuator device.

FIG. 16 shows a graphical comparison of the force-velocity relationship of a parallel actuator device to lever motors. Line 160 represents the force-velocity relationship of parallel actuator device 120 with actuating elements 127 and 128 disposed in parallel between movable body 125 and base body 126. Line 160 shows an example of the force-velocity relationship for a single input position of parallel actuator device 120. Parallel actuator device 120 has many input positions due to the changing position of movable body 125, and thus, has many force-velocity relationship curves. Line 160 shows an example of one force-velocity curve for a particular position of parallel actuator device 120. Because many different force-velocity curves are available for parallel actuator device 120, the optimal force-velocity curve for a particular task can be selected.

A single actuator used in a powered prosthetic device, such as in a lever motor design, has a linear force-velocity relationship. Line 162 shows an example of a single DC motor used in a lever motor design. The approximate force-velocity relationship of the single motor, shown by line 162, indicates the motor velocity and force have a linear relationship. Line 164 shows an approximate force-velocity relationship of a larger single DC motor or multiple smaller DC motors combined in series. The force-velocity relationships of the smaller motor (line 162) and larger motor (line 164) show that a larger motor provides higher force and velocity, but the force-velocity relationship remains linear.

Skeletal muscle performs with high stall force and high velocity, with a force-velocity curve taking the form of a rectangular hyperbola. If a single motor is selected with the same peak power as a muscle, the motor will have a lower stall force and a lower maximum velocity than the muscle. If a motor is selected with the same stall load and maximum velocity as a muscle, the motor will have a higher peak power and will need to be a much larger motor, and therefore, a much heavier motor. A heavier motor in a prosthetic device is undesirable, because the weight of the motor becomes too heavy for the user to wear.

Parallel actuator device 120 combines actuating elements 127 and 128 in a kinematically redundant parallel arrangement to produce a force-velocity relationship that behaves more similarly to a human skeletal muscle. The force-velocity curve, shown as line 160, for parallel actuator device 120 is achieved by the extra degree of freedom at the input. The extra degree of freedom within parallel actuator device 120 allows the position of movable body 125 to be selected to control the input to output transmission ratio of parallel actuator device 120. Passive linking member 129 is coupled to movable body 125 such that a particular output velocity and force measured at passive linking member 129 is available for many different input positions of movable body 125. The internal geometry of parallel actuator device 120 is selected to combine actuating elements 127 and 128 to provide, for example, high force at low velocity or high velocity at low load. The benefit of selecting a geometry and a force-velocity curve with high force at low velocity is that parallel actuator device 120 performs heavy lifting at low speeds, for example, when the user stands up from a sitting position. Parallel actuator device 120 with internal geometry and a force-velocity curve with high velocity at low load allows the user to move quickly, such as when running. Therefore, parallel actuator device 120 performs well over an increased range of velocity and force and more like a human skeletal muscle compared to a single motor having a similar power.

The force-velocity curve of skeletal muscle changes with output position as the muscle fiber length deviates shorter or longer than optimal. Accordingly, skeletal muscle performance is highly dependent on joint position. In contrast, parallel actuator device 120 performance is independent of output position. Parallel actuator device 120 performance is largely independent of the output position of passive linking member 129. Therefore, the independent nature of motor torque and shaft angle for actuating elements 127 and 128 allows for the force-velocity performance of parallel actuator device 120 to exceed that of skeletal muscle. Another advantage of parallel actuator device 120 is that the device is still able to function as a lever motor if one of actuating elements 127 or 128 fails. Either actuating element 127 or actuating element 128 actuates to move passive linking member 129 in both the hip extension and hip flexion directions.

Unlike a single motor system with a linear force-velocity curve, parallel actuator device 120 with a non-linear force-velocity curve achieves a higher force and higher velocity with a lower peak power requirement. For example, parallel actuator device 120 has actuating elements 127 and 128 disposed in parallel where each actuating element 127 and 128 includes a 150 W DC motor. Parallel actuator device 120 achieves both a higher force and a higher velocity than a lever motor design having a single 300 W DC motor. A single motor would need to be approximately five to ten times larger than the motors in parallel actuator device 120 to produce a similar force and velocity output as parallel actuator device 120. Therefore, the single motor would be much heavier and have a greater inertia than actuating element 127 and 128 of parallel actuator device 120. A user would have difficulty moving the heavier motor, which would reduce the velocity available to the user by simply being too heavy to move quickly. Because smaller motors are used in parallel actuator device 120, the prosthetic device is lighter in weight and is more comfortable for the user. A lighter weight mechanism is also more efficient than heavier designs and further improves the performance of the prosthetic device.

Like active compliant parallel device 900 parallel actuator device 120 is employed in a variety of applications. Parallel actuator device 120 can be applied to prosthetic, orthotic, or robotic devices that require actuation of joints for locomotion, necessitate high force and speed from lightweight devices, or require actuation of a limb. Parallel actuator device 120 applies to fields using devices that have robotic end effectors, which interact with unstructured or unpredictable environments.

While one or more embodiments of the present invention have been illustrated in detail, the skilled artisan will appreciate that modifications and adaptations to those embodiments may be made without departing from the scope of the present invention as set forth in the following claims.

What is claimed:

1. A method of making a prosthetic joint device, comprising:
   providing a base body;
   providing a movable body;
   disposing a first linking member connected between a first movable joint of the movable body and a first movable joint of the base body;
   disposing a second linking member connected between a second movable joint of the movable body and a second movable joint of the base body; and
   disposing a prosthetic foot connected to a third movable joint of the movable body and further connected to a third movable joint of the base body to provide rotation of the prosthetic foot with respect to the base body.

2. The method of claim 1, wherein the first linking member or second linking member includes an actuator.

3. The method of claim 1, wherein the first linking member or second linking member includes a compliant member.

4. The method of claim 1, wherein the first linking member or second linking member includes a first actuator or the second linking member includes a compliant member.

5. The method of claim 1, wherein the second movable joint of the movable body is disposed between the first movable joint of the movable body and third movable joint of the movable body.

6. The method of claim 1, wherein the first movable joint of the base body, the second movable joint of the base body, and the third movable joint of the base body each include a revolute joint.

7. The method of claim 1, wherein the first movable joint of the movable body, second movable joint of the movable body, and third movable joint of the movable body each include a revolute joint.

8. A prosthetic joint device, comprising:
   a base body;
   a movable body;
   a first linking member connected between a first rotational joint of the movable body and a first rotational joint of the base body;
   a second linking member connected between a second rotational joint of the movable body and a second rotational joint of the base body; and
   a prosthetic foot connected to a third rotational joint of the movable body and further connected to a third rotational joint of the base body to provide rotation of the prosthetic foot with respect to the base body.

9. The prosthetic joint device of claim 8, wherein the first linking member or second linking member includes an actuator.

10. The prosthetic joint device of claim 8, wherein the first linking member or second linking member includes a compliant member.

11. The prosthetic joint device of claim 8, wherein the first linking member includes a first actuator and the second linking member includes a compliant member.

12. The prosthetic joint device of claim 8, wherein the second rotational joint of the movable body is disposed between the first rotational joint of the movable body and third rotational joint of the movable body.

13. The prosthetic joint device of claim 8, wherein the first rotational joint of the base body, the second rotational joint of the base body, and the third rotational joint of the base body each include a revolute joint, and the first rotational joint of the movable body, second rotational joint of the movable body, and third rotational joint of the movable body each include a revolute joint.

14. A method of making a prosthetic joint device, comprising:
   providing a base body;
   providing a movable body;
   disposing an actuator connected between a first joint of the movable body and a first joint of the base body;
   disposing a compliant member connected between a second joint of the movable body and a second joint of the base body; and
   disposing a prosthetic foot connected to a third rotational joint of the movable body and further connected to a third joint of the base body to provide rotation of the prosthetic foot with respect to the base body.

15. The method of claim 14, wherein the second joint of the movable body is disposed between the first joint of the movable body and third rotational joint of the movable body.

16. The method of claim 14, wherein the first joint of the base body, the second joint of the base body, and the third joint of the base body each include a revolute joint.

17. The method of claim 14, wherein the first joint of the movable body, second joint of the movable body, and third rotational joint of the movable body each include a revolute joint.

18. The method of claim 14, wherein the compliant member includes a spring.

19. The method of claim 14, wherein the actuator includes a motor-driven screw or piston.

20. A prosthetic joint device, comprising:
a base body;
a movable body;
an actuator connected between a first joint of the movable body and a first joint of the base body;
a compliant member connected between a second joint of the movable body and a second joint of the base body; and
a prosthetic foot connected to a third movable joint of the movable body and further connected to a third joint of the base body to provide rotation of the prosthetic foot with respect to the base body.

21. The prosthetic joint device of claim 20, wherein the second joint of the movable body is disposed between the first joint of the movable body and third movable joint of the movable body.

22. The prosthetic joint device of claim 20, wherein the first joint of the base body, the second joint of the base body, and the third joint of the base body each include a revolute joint, and the first joint of the movable body, second joint of the movable body, and third movable joint of the movable body each include a revolute joint.

23. The prosthetic joint device of claim 20, wherein the compliant member includes a spring.

24. The prosthetic joint device of claim 20, wherein the actuator includes a motor-driven screw or piston.

25. The prosthetic joint device of claim 20, wherein the prosthetic foot includes a flat bottom portion.

* * * * *

UNITED STATES PATENT AND TRADEMARK OFFICE
CERTIFICATE OF CORRECTION

| | |
|---|---|
| PATENT NO. | : 10,575,970 B2 |
| APPLICATION NO. | : 15/379815 |
| DATED | : March 3, 2020 |
| INVENTOR(S) | : Matthew Aaron Holgate |

Page 1 of 1

It is certified that error appears in the above-identified patent and that said Letters Patent is hereby corrected as shown below:

In the Specification

In Column 8 at Line 39, after "10" insert --,--.

In Column 14 at Line 23, delete "member" and insert --element--.

In Column 17 at Line 6, delete "27" and insert --27,--.

In Column 17 at Line 17, delete "0.25" and insert --0.250--.

In Column 17 at Line 25, delete "27" and insert --27,--.

In Column 17 at Line 28, delete "27" and insert --27,--.

In Column 17 at Line 37, delete "27" and insert --27,--.

In Column 18 at Line 10, delete "900" and insert --900,--.

In Column 19 at Line 22, delete "131a and 131b." and insert --130a and 130b.--.

In Column 19 at Line 23, delete "131a" and insert --130a--.

In Column 21 at Line 66, delete "131a" and insert --130a--.

In Column 21 at Line 67, delete "-130f," and insert --130f,--.

In the Claims

In Column 25 at Lines 66-67, in Claim 4, delete "second linking member includes a first actuator or" and insert --includes a first actuator and--.

Signed and Sealed this
Fourth Day of August, 2020

Andrei Iancu
*Director of the United States Patent and Trademark Office*